United States Patent
Stevens et al.

(10) Patent No.: US 6,802,319 B2
(45) Date of Patent: *Oct. 12, 2004

(54) MINIMALLY-INVASIVE DEVICES AND METHODS FOR TREATMENT OF CONGESTIVE HEART FAILURE

(76) Inventors: John H. Stevens, 727E Lona Verde Ave., Palo Alto, CA (US) 94303; Lee R. Bolduc, 761-1/2 Palo Alto Ave., Mountain View, CA (US) 94041; Stephen W. Boyd, 333 Palomar Dr., Redwood City, CA (US) 94062; Brian S. Donlon, 13944 Fremont Pines, Los Altos Hills, CA (US) 94022; Hanson S. Gifford, III, 3180 Woodside Rd., Woodside, CA (US) 94062; Philip R. Houle, 525 Homer Ave., Apt. #8, Palo Alto, CA (US) 94301; Daniel C. Rosenman, 1415 Waller St. #3, San Francisco, CA (US) 94117

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 101 days.

This patent is subject to a terminal disclaimer.

(21) Appl. No.: 09/535,141

(22) Filed: Mar. 24, 2000

(65) Prior Publication Data

US 2003/0102000 A1 Jun. 5, 2003

Related U.S. Application Data

(63) Continuation of application No. 08/685,262, filed on Jul. 23, 1996, now Pat. No. 6,125,852, which is a continuation-in-part of application No. 08/485,600, filed on Jun. 7, 1995, now abandoned, which is a continuation-in-part of application No. 08/281,962, filed on Jul. 28, 1994, now abandoned, which is a continuation-in-part of application No. 08/163,241, filed on Dec. 6, 1993, now Pat. No. 5,571,215, which is a continuation-in-part of application No. 08/023,778, filed on Feb. 22, 1993, now Pat. No. 5,452,733.

(51) Int. Cl.$^7$ ............................................... A61B 19/00
(52) U.S. Cl. ........................................................ 128/898
(58) Field of Search .......................... 128/898; 623/1.11, 623/2.11, 11; 604/4, 5, 6; 600/16, 17, 18

(56) References Cited

U.S. PATENT DOCUMENTS

| 3,409,013 A | 11/1968 | Berry |
| 4,042,979 A | 8/1977 | Angell |

(List continued on next page.)

FOREIGN PATENT DOCUMENTS

| DE | 3614292 | 11/1987 |

(List continued on next page.)

OTHER PUBLICATIONS

US 6,197,052, 6/2001, Cosgrove et al. (withdrawn)

(List continued on next page.)

Primary Examiner—David J. Isabella

(57) ABSTRACT

A method of treatment of congestive heart failure comprises the steps of introducing an aortic occlusion catheter through a patient's peripheral artery, the aortic occlusion catheter having an occluding member movable from a collapsed position to an expanded position; positioning the occluding member in the patient's ascending aorta; moving the occluding member from the collapsed shape to the expanded shape after the positioning step; introducing cardioplegic fluid into the patient's coronary blood vessels to arrest the patient's heart; maintaining circulation of oxygenated blood through the patient's arterial system; and reshaping an outer wall of the patient's heart while the heart is arrested so as to reduce the transverse dimension of the left ventricle. The ascending aorta may be occluded and cardioplegic fluid delivered by means of an occlusion balloon attached to the distal end of an elongated catheter positioned transluminally in the aorta from a femoral, subclavian, or other appropriate peripheral artery.

10 Claims, 15 Drawing Sheets

U.S. PATENT DOCUMENTS

| | | |
|---|---|---|
| 4,173,981 A | 11/1979 | Mortensen |
| 4,192,293 A | 3/1980 | Asrican |
| 4,261,342 A | 4/1981 | Aranguren Duo |
| 4,372,293 A | 2/1983 | Vijil-Rosales |
| 4,409,974 A | 10/1983 | Freedland |
| 4,536,893 A | 8/1985 | Parravicini |
| 4,655,218 A | 4/1987 | Kulik et al. |
| 4,690,134 A | 9/1987 | Snyders |
| 4,705,040 A | 11/1987 | Mueller et al. |
| 4,808,163 A | 2/1989 | Laub |
| 4,936,857 A | 6/1990 | Kulik |
| 4,944,753 A | 7/1990 | Burgess et al. |
| 4,960,424 A | 10/1990 | Grooters |
| 4,997,431 A | 3/1991 | Isner et al. |
| 5,011,469 A | 4/1991 | Buckberg et al. |
| 5,032,128 A | 7/1991 | Alonso |
| 5,041,130 A * | 8/1991 | Cosgrove et al. .......... 623/2.11 |
| 5,104,393 A * | 4/1992 | Isner et al. .................. 606/15 |
| 5,104,407 A | 4/1992 | Lam et al. |
| 5,106,386 A | 4/1992 | Isner et al. |
| 5,109,859 A | 5/1992 | Jenkins |
| 5,131,905 A | 7/1992 | Grooters |
| RE34,021 E * | 8/1992 | Mueller et al. ............. 604/533 |
| 5,169,381 A | 12/1992 | Snyders |
| 5,188,619 A | 2/1993 | Myers |
| 5,192,341 A | 3/1993 | Ehrler |
| 5,197,979 A | 3/1993 | Quintero et al. |
| 5,203,776 A | 4/1993 | Durfee |
| 5,250,038 A | 10/1993 | Melker et al. |
| 5,250,049 A | 10/1993 | Michael |
| 5,284,488 A | 2/1994 | Sideris |
| 5,308,320 A * | 5/1994 | Safar et al. ................ 604/6.14 |
| 5,312,344 A | 5/1994 | Grinfeld et al. |
| 5,332,402 A | 7/1994 | Teitelbaum |
| 5,339,800 A | 8/1994 | Wiita et al. |
| 5,385,528 A | 1/1995 | Wilk |
| 5,391,156 A | 2/1995 | Hildwein et al. |
| 5,433,700 A | 7/1995 | Peters |
| 5,433,727 A | 7/1995 | Sideris |
| 5,450,860 A | 9/1995 | O'Connor |
| 5,452,733 A * | 9/1995 | Sterman et al. ............. 128/898 |
| 5,458,574 A | 10/1995 | Machold et al. |
| 5,496,305 A | 3/1996 | Kittrell et al. |
| 5,501,698 A * | 3/1996 | Roth et al. .................. 606/205 |
| 5,509,428 A | 4/1996 | Dunlop |
| 5,533,958 A | 7/1996 | Wilk |
| 5,571,215 A * | 11/1996 | Sterman et al. |
| 5,584,803 A * | 12/1996 | Stevens et al. ............ 604/6.16 |
| 5,593,424 A | 1/1997 | Northrup III |
| 5,665,092 A | 9/1997 | Mangiardi et al. |
| 5,682,906 A * | 11/1997 | Sterman et al. ............. 128/898 |
| 5,713,954 A | 2/1998 | Rosenberg et al. |
| 5,718,725 A | 2/1998 | Sterman et al. |
| 5,758,663 A | 6/1998 | Wilk et al. |
| 5,766,151 A * | 6/1998 | Valley et al. .......... 604/103.07 |
| 5,776,151 A | 7/1998 | Chan |
| 5,800,334 A | 9/1998 | Wilk |
| 5,800,528 A | 9/1998 | Lederman et al. |
| 5,810,721 A * | 9/1998 | Mueller et al. ............. 600/206 |
| 5,814,097 A | 9/1998 | Sterman et al. |
| 5,849,005 A | 12/1998 | Garrison et al. |
| 5,855,601 A | 1/1999 | Bessler et al. |
| 5,856,614 A | 1/1999 | Hall |
| 5,865,791 A | 2/1999 | Whayne et al. |
| 5,957,977 A | 9/1999 | Melvin |
| 5,971,911 A | 10/1999 | Wilk |
| 5,972,030 A | 10/1999 | Garrison et al. |
| 5,984,857 A | 11/1999 | Buck et al. |
| 6,024,756 A | 2/2000 | Huebsch et al. |
| 6,079,414 A | 6/2000 | Roth |
| 6,117,159 A | 9/2000 | Huebsch et al. |
| 6,125,852 A * | 10/2000 | Stevens et al. ............. 128/898 |
| 6,182,664 B1 | 2/2001 | Cosgrove |
| 6,217,610 B1 | 4/2001 | Carpentier et al. |
| 6,221,103 B1 | 4/2001 | Melvin |
| 6,224,540 B1 | 5/2001 | Lederman et al. |
| 6,258,021 B1 | 7/2001 | Wilk |
| 6,283,993 B1 | 9/2001 | Cosgrove et al. |
| 2001/0003986 A1 | 6/2001 | Cosgrove |
| 2002/0007216 A1 | 1/2002 | Melvin |
| 2002/0022880 A1 | 2/2002 | Melvin |
| 2002/0029783 A1 | 3/2002 | Stevens et al. |
| 2002/0111533 A1 | 8/2002 | Melvin |

FOREIGN PATENT DOCUMENTS

| | | |
|---|---|---|
| DE | 4234127 | 5/1994 |
| EP | 0218275 A1 | 4/1987 |
| EP | 0583012 A1 | 2/1994 |
| WO | WO 91/19465 | 12/1991 |
| WO | WO 93/20741 | 10/1993 |
| WO | WO 93/20742 | 10/1993 |
| WO | WO 95/06447 | 3/1995 |
| WO | WO 95/16476 | 6/1995 |
| WO | WO 9604852 A1 | 2/1996 |
| WO | WO 96/40356 | 12/1996 |
| WO | WO 97/24082 | 7/1997 |
| WO | WO 97/24083 | 7/1997 |

OTHER PUBLICATIONS

Huikuri, H. V., "Effect of mitral valve replacement on left ventricular function in mitral regurgitation", Br Heart F 1983; 49: pp. 328–333.

Pitarys II, C. J., et al., "Long–Term Effects of Excision of the Mitral Apparatus on Global and Regional Ventricular Function In Humans", JACC, vol. 15, No. 3, Mar. 1, 1990, pp. 557–563.

Bolling, S. F., "Early Outcome of Mitral Valve Reconstruction in Patients with End–Stage Cardiomyopathy", The Journal of Thoracic and Cardiovascular Surgery, vol. 109, No. 4, pp. 676–683.

Oe, Masahiro, et al., "Effects of preserving mitral apparatus on ventricular systolic function in miral valve operations in dogs", The Journal of Thoracic and Cardiovascular Surgery, vol. 106, No. 5, pp. 1138–1146.

Alonso–Lej, F., "Adjustable Annuloplasty for Tricuspid Insufficiency", The Annuals of Thoracic Surgery, vol. 46, No. 3, Sep. 1998, pp. 368–369.

Kurjansky, P., et al., "Adjustable Annuloplasty for Tricuspid Insufficiency", Annual Thoracic Surgery, vol. 44, Oct. 1987, pp. 404–406.

Boyd, A. D., et al., "Tricuspid annuloplasty", The Journal of Thoracic and Cardiovascular Surgery, vol. 68, No. 3, Sep. 1974, pp. 344–351.

Edie, R. N.., et al., "Surgical repair of single ventricle", The Journal of Thoracic and Cardiovascular Surgery, vol. 66, No. 3, Sep. 1973, pp. 350–360.

McGoon, D. C., et al., "Correction of the univentricular heart having two atrioventricular valves" The Journal of the Thoracic and Cardiovascular Surgery, vol. 74, No. 2, Aug. 1977, pp. 218–226.

Lev, M., et al., "Single (Primitive) Ventricle", Circulation, vol. XXXIX, May. 1969, pp. 577–591.

Shumacker, Jr., H. B., "Cardiac Aneurysms", The Evolution of Cardiac Surgery, vol. 21, 1992, pp. 159–165.

Feldt, R. H., et al.,"Current status of the septation procedure for univentricular heart", The Journal of Thoracic and Cardiovascular Surgery, vol. 82, No. Jul. 1981, pp. 93–97.

Doty, D. B., et al., "Septation of the univentricular heart", The Journal of Thoracic and Cardiovascular Surgery, vol. 78, No. 3, Sep. 1979, pp. 423–430.

Savage, E. B., et al., "Repair of left ventricular aneurysm, Changes in ventricular mechanics, hemodynamics, and oxygen consumption", The Journal of Thoracic and Cardiovascular Surgery, vol. 134, No. 3, Sep. 1992, pp. 752–762.

Melvin, D., "Ventricular Radius–Reduction Without Resection", A Computational Assessment, University of Cincinnati.

Melvin, D. B., et al., "Reduction of Ventricular Wall Tensile Stress by Geometric Remodeling Device", University of Cincinnati and CardioEnergetics, Inc., (Poster text, ASAIO, 1999).

Kay, E. B., et al., "Surgical Treatment of Mitral Insufficiency", The Journal of Thoracic Surgery, vol. 29, Jan–Jun, 1955, pp. 618–620.

Harken, D. E., et l., "The Surgical Correction of Mitral Insufficiency", The Journal of Thoracic Surgery, vol. 28, Jul–Dec, 1954, pp. 604–627.

Bailey, C. P., et al., "Closed Intracardiac Tactile Surgery", Diseases of the Chest, vol. XXII, Jul–Dec, 1952, pp. 1–24.

Sakakibara, S., "A Surgical Approach to the Correction of Mitral Insufficiency", Annais of Surgery, vol. 142, Jul–Dec 1955, pp. 196–203.

Glenn, W. W. L., et al.,"The Surgical Treatment of Mitral Insufficiency: The Fate of A Vascularized Transchamber Intracardiac Graft", Annals of Surgery, vol. 141, No. 4, pp. 510–518.

Kay, E. B., et al., "Surgical Treatment of Mitral Insufficiency", Surgery, vol. 37, No. 5, May, 1995, pp. 697–620.

Bailey, C. P., et al., "The Surgical Correction of Mitral Insufficiency By the Use of Pericardial Grafts", The Journal of Thoracic Surgery, vol. 28, Jul–Dec 1954, pp. 551–603.

Harken, D. E., et al., "The Surgical Correction of Mitral Insufficiency", The Journal of Thoracic Surgery, vol. 28, Jul–Dec 1954, pp. 604–627.

Shumacker, Jr., H.B., "Attempts to Control Mitral Regurgitation", The Evolution of Cardiac Surgery, 1992, pp. 204–210.

Ianuzzo, C. D., et al., "Preservation of the Latissimus Dorsi Muscle During Cardimyoplasty Surgery ", Journal of Cardiac Surgery, vol. 11, Sep. 1996, pp. 99–108.

Chachques, J. C., et al., "Latissimus Dorsi Dynamic Cardiomyoplasty", The cosiety of Thoracic Surgeons, 1989, vol. 47, pp. 600–604.

Moreira, L. F. P., et al. "Latissimus Dorsi Cardiomyoplasty in the Treatment of Patients with Dilated Cardiomyopathy", Circulation, 1990, vol. 82.

Lucas, C. M. B., et al., "Long–Term Follow–Up (1 to 35 Weeks) After Dynamic Cardiomyoplasty", Journal of American College of Cardiology, vol. 22, No. 3, Sep. 1993, pp. 758–767.

Batista, R. J. V., et al., "Partial Left Ventrienlectomy to Improve Left Ventricular Function in End–Stage Heart Disease", Journal of Cardiac Surgery, 1996; II: pp. 96–67.

Kormos, R. L., et al.,"Experience with Univentricular Support in Mortally III Cardiac Transplant Candidates", Ann. Thorac. Surg. 1990; 49; pp. 261–272.

Wampler, R. K., et al., "Treatment of Cardiogenic Shock with the Hemopump Left Ventricular Assist Device", Ann. Thorac. Surg. 1991; 52; pp. 506–513.

McCarthy, P. M., et al., "Clinical experience with the Novacor ventricular assist system", J. Thorac. Cardiovasc. Surg. 1991; 102: pp. 578–587.

Bearnson, G. B., et al., "Development of a Prototype Magnetically Suspended Ventricular Assist Device", ASAIO Journal, Jul–Aug 1996, vol. 42, No. 4pp. 275–281.

Sakakibara, N., et al., "A Muscle Powered Cardiac Assist Device for Right Ventricular Support: Total Assist or Partial Assist?", ASAIO Transcactions, Jul–Sep 1990, vol. 36, No. 3, pp. M372–M375.

Bach, D. S., et al., "Early improvement in congestive heart failure after corection of secondary mitral regurgitation in end–stage cardiomyopathy", American Heart Journal, Jun 1995, vol. 129, No. 6, pp. 1165–1170.

Farrar, D. J., et al., "A New Skeletal Muscle Linear–pull Energy Convertor as a Power Source for Prostheic Circulatory Support Devices", The Journal of Heart and Lung Transplantation, Sep/Oct 1992, vol. 11, No. 5, pp. S341–S349.

ABIOMED, Annual Report, 1996, for the Fiscal Year Ending Mar. 31, 1996.

Medtronic 1996 Annual Shareholders Report.

Invited Commentary: Preservation of Muscle During Surgery, pp. 109–110, On "Preconditioning of Skeletal Muscle: Application to Dynamic Cardiomyoplasty" by C. David Ianuzzo, et al.

Ozuner, Gokhan, et al. "Creation of Pericardial Window Using Thoracoscopic Techniques"Surg. Gynecology & Obstetrics 1992; 175:69–71.

Wakabayashi, Akio. "Expanded Applications of Diagnostic and Therapeutic Thoracoscopy" J Thorac and Cardiovasc Surg 1991; 102:721–3.

Yamaguchi, A. et al. "A Case of a Reoperation Using a Balloon Catheter With Blocked Pars Acendes Aortae, " Kyobu Geka, Oct. 1991, 42:11:961–964.

Peters, W. S., MB, "Minimally Invasive Cardiac Surgery by Cardioscopy, " AustralAs J Cardio Thorac Surg 1993:29(3) 152–154.

Cohn, L. H. et al. "Right Thoracotomy, Femorofemoral Bypass, and Deep Hypothermia for Re–replacement of the Mitral Valve, " Ann. Thorac. Surg. 1989; 48; 69–71.

Fundaro, P. et al. "Towards an easier and safer reoperation of the Atrioventricular valves The right Anterolateral Thoracotomy approach without pericardial dissection, " J. Cardiovasc. Surg. 30, 1989, 779–781.

Tribble, C. G. et al. "Anterolateral Thoracotomy as an Alternative to Repeat Median Sternotomy for Replacement of the Mitral Valve, " Ann. Thorac. Surg. 43:380–382, Apr. 1987.

Berreklouw, E. et al. "Revival of Right Thoracotomy to Approach Atrio–ventricular Valves in Reoperations, "Thorac. cardiovasc. Surgeon 32 (1984) 331–333.

Cosgrove, D. M. "Management of the Calcified Aorta: An Alternative Method of Occlusion" Ann Thorac Surg. 36:718–719 (1983).

J. H. Foster and J. B. Threlkel "Proximal Control of Aorta with a Balloon Catheter" Surg, Gynecology & Obstetrics pp. 693–694 (1971).

H. G. Erath, Jr. and Wiiliam S. Stoney, Jr. "Balloon Catheter Occlusion of the Ascending Aorta" Ann Thorac Surg. 35:560–561 (1983).

Sakaguchi, H. et al., "Aortic Valve Replacement and Coronary Artery Bypass" J. Japanese ssoc. for Thoracic Surgery 41(6):1063–1068 (1993).

Reversible Cardiomyopathy, 88 Days of Biventricular VAD Support as a Bridge to Recovery, Thoratec's Heartbeat, vol. 10.2, Aug. 1996.

Gundry et al. "A Comparison of Retrograde Cardioplegia Versus Antegrade Cardioplegia in the Presence of Coronary Artery Obstruction, " Ann. Thorac. Surg., Aug. 1984, 38:2, 124–127.

Lust et al. "Improved Protection of Chronically Inflow–limited Myocardium with Retrograde Coronary Sinus Cardioplegia, " Circulation III, Nov. 1988, 78:5, 217–223.

Crooke et al., "Biventricular Distribution of Cold Blood Cardioplegic Solution Administered by Different Retrograde Techniques, " J. Cardiac Thorac. Surg., 1991, 102:4, 631–636.

Sabiston, D. C., Textbook of Surgery, 10th Ed., 1972, pp. 2021–2023, pp. 2114–2121.

Buckberg, G. D., "Strategies and Logic of Cardioplegic Delivery to Prevent, Aoid, and Reverse Ischemic and Reperfusion Damage, " J. Thorac. Cardio. Vasc. Surg., 1987, 93:127–139.

Razi, D. M. "The Challenge of Calcific Aortitis, " J. Cardiac Thorac. Surg., 1993, 8:102–107.

Coltharp, William H., et al. "Videothorascopy . . . " Ann Thorac Surg 1992; 53:776–9.

Jamieson, W. R. Eric. "Modern Cardiac Valve Devices–Bioprotheses and Mechanical Prostheses" J Card Surg. 1993;8: 89–98.

Landrenseau, Rodney J., et al. "Video–Assisted Thoracic Surgery . . . " Ann Thorac Surg 1992; 54:800–7.

Mack, Michael J., et al. "Present Role of Thoracoscopy in the Diagnosis and Treatment of Diseases of the Chest" Ann Thorac Surg 1992; 54:403–9.

Magovern, George J. "Sutureless Aortic and Mitral Prosthetic Valves" J. Thoracic and Cardiovasc Surg 1964; 48(3): 346–361.

Carpentier, A., et al., "Myocardial Substitution with a Stimulated Skeletal Muscle: First Successful Clinical Case", Letters to the Editor, p. 1267, Sep. 1996.

"Congestive Heart Failure in the United States: A New Epidemic", NHLBI Congestive Heart Failure Data Fact Sheet, National Heart, Lung, and Blood Institute, National Institutes of Health, http://www.nhi.gov/nhlbi/cardio/other/gp/CHF:htm.

"Heartmate System Becomes First Implantable Cardiac–Assist Device to be Approved to Commercial Sale in the U.S., Study Shows New Artificial Heart Technology Can Double The Rate of Survival for Heart Transplant Candidates", TCI Thermo Cardiosystems Inc. News Release, Oct. 3, 1994.

Abiomed News, For Immediate Release, Abiomed Wins $8.5 Million Federal Contract To Qualify its Artifical Heart for Human Trials, Sep. 16, 1996.

Abiomed News For Immediate Release, Abiomed'Temporary Artificial Heart System Reaches 200 U.S. Medical Center Milestone, Sep. 26, 1996.

Abiomed News, For Immediate Release, Abiomed Wins $4.35 Million Contract From the National Heart, Lung and Blood Institutes to Develop Implantable Heart Booster, Oct. 3, 1995.

Abiomed News, For Immediate Release, Abiomed Wins NIH Grant to Develop Calcification–Resistant Plastic Heart Valve, Sep. 29, 1995.

Abiomed News, Abiomed Wins Research Grant From NIH to Develop Suturing Instrument for Abdominal Surgery, Aug. 25, 1995.

Abiomed News, For Immediate Release, Abiomed Receives Grant from NIH to Develop Disposable Bearingless Centrifugal Blood Pump, Aug. 11, 1995.

Abiomed News, Abiomed Receives Grant From National Institutes of Health To Develop a Laser Welding Technique for Tissue Repair, Jun. 9, 1995.

Abiomed News, For Immediate Release, Abiomed®'s Temporary Artificial Heart System Reaches 1,000 patient Milestone; BVS–5000® in More than 100 U.S. Medical Centers, Apr. 27, 1995.

Thoratec™ Brochure, Jan. 2, 1997.

Batista et al., "Partial Left Ventriculectomy to Improve Left Ventricular 8Function in End–Stage Heart Disease", vol. 11, No. pp. 96–98, Jul. 1992.

Schuler, G., et al., "Temporal Response of Left Ventricular Performance to Mitral Valve Surgery", Circulation, vol. 59, No. 6 Jun. 1979, pp. 1218–1231.

Abiomed News, For Immediate Release, Abiomed Receives FDA Approval To Expand Indications For Use of Cardiac Assist System, May 17, 1996.

Ogawa, K., et al., "Aortic Arch Reconstruction Without Aortic Cross–Clamping Using Separate Extracorporeal Circulation", J. Jpn. Assn. Thorac. Surg., 1993; 41: 2185–2190, with English language abstracts.

Ishikawa, M., "Myocardial Protection by Retrograde Cardiac Perfusion with Cold Medified Krebs Solution Through Coronary Sinus During Complete Ischemic Arrest for 120 Min. ", J. Jpn. Assn. Thorac. Surg., 1977, 25:12, 1592–1601, with English language abstracts;.

Takahashi, M., "Retrograde Coronary Sinus Perfusion for Myocardial Protection in Aortic Valve Surgery", J. Jpn. Assn. Thorac. Surg., 1982, 30:3 306–318, with English Language abstracts.

* cited by examiner

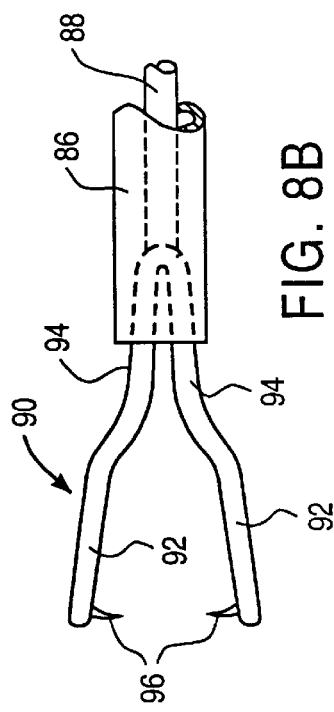
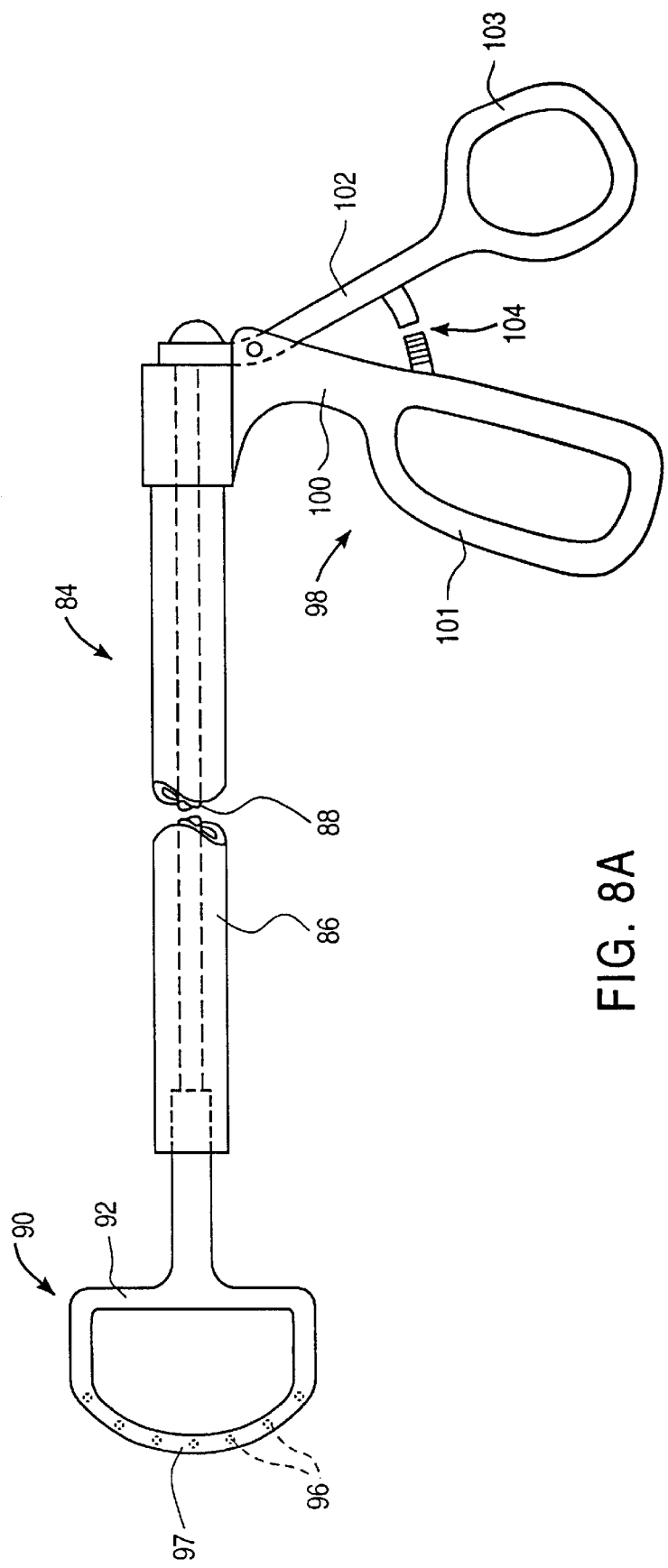
FIG. 8B
FIG. 8A

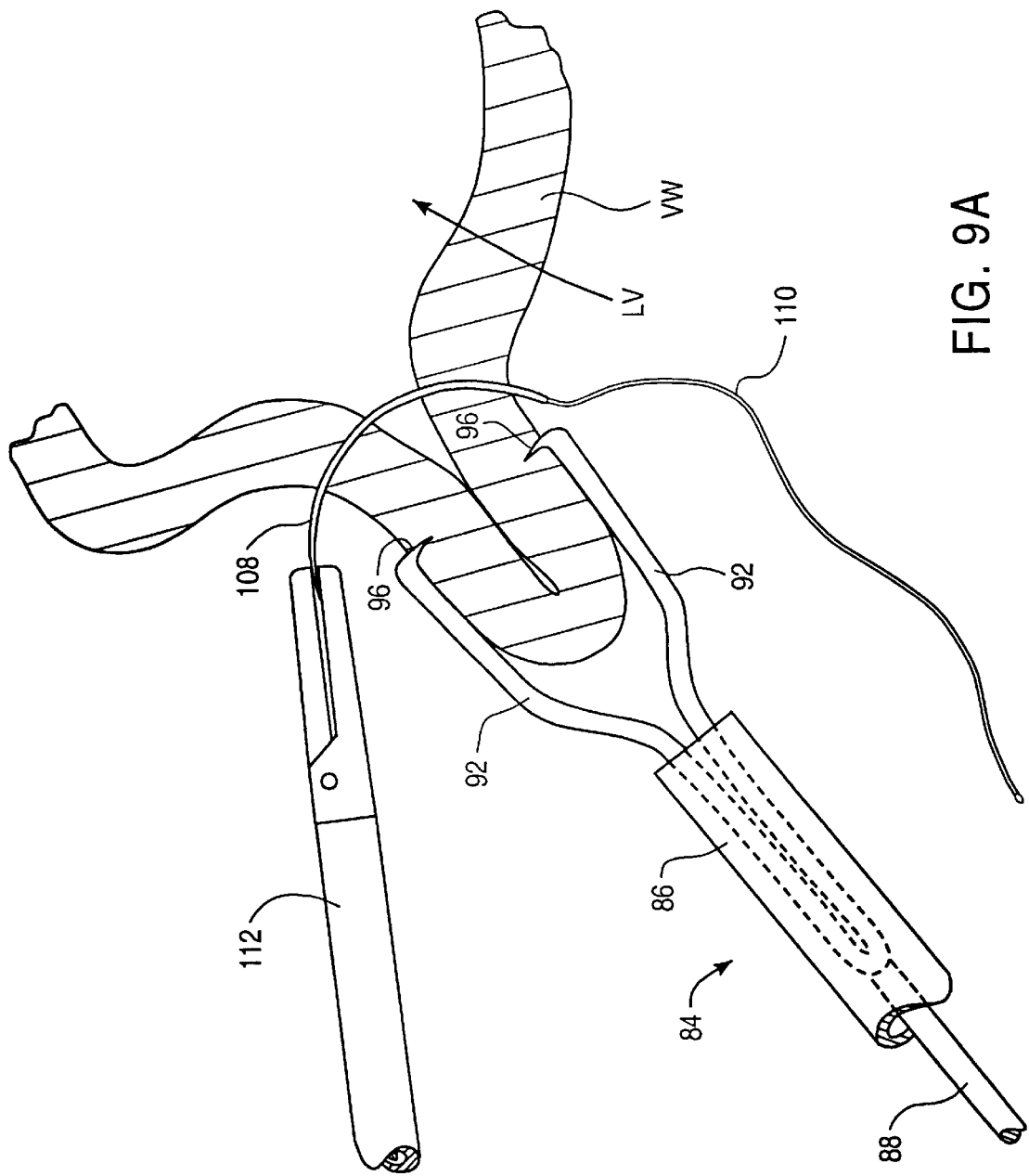

MINIMALLY-INVASIVE DEVICES AND METHODS FOR TREATMENT OF CONGESTIVE HEART FAILURE

CROSS-REFERENCES TO RELATED APPLICATIONS

This application is a Continuation of U.S. patent application Ser. No. 08/685,262, filed Jul. 23, 1996, now U.S. Pat. No. 6,125,852, which is a Continuation-In-Part of application Ser. No. 08/485,600, filed Jun. 7, 1995, now abandoned, which is a Continuation-In-Part of application Ser. No. 08/281,962, filed Jul. 28, 1994, now abandoned, which is a Continuation-In-Part of application Ser. No. 08/163,241, filed Dec. 6, 1993, now U.S. Pat. No. 5,571,215, which is a Continuation-In-Part of application Ser. No. 08/023,778, filed Feb. 22, 1993, now issued as U.S. Pat. No. 5,452,733, the complete disclosures of which are hereby incorporated herein by reference for all purposes.

BACKGROUND OF THE INVENTION

In congestive heart failure or CHF, the heart has become so enlarged as a result of viral infection, myocardial infarction or other disease that it is unable to pump at a sufficient rate to maintain adequate circulation of blood throughout the body. As a result, blood backs up into the lungs, causing shortness of breath and other symptoms, and, if left untreated, the disease can lead to death.

For some patients, the CHF may be treated effectively with medication. However, in many cases, the disease progresses to a point at which the patient requires a heart transplant. Unfortunately, due to a donor shortage, of the 40,000 patients who may require a transplant each year, only 2500 actually get one, with up to 15–20% of patients dying while on the waiting list for a donor heart.

In response to the need for alternatives to transplant for treating CHF, a surgical procedure has been tried in recent years known as the "Batista Operation" after its developer, Dr. Randas J. V. Batista. In this procedure, a large section of the left ventricular wall is excised from the heart and the wall then sewn back together, thereby reducing the transverse dimension and volume of the left ventricle, the primary pumping chamber of the heart. The reduced volume of the ventricle permits less blood to be present in the chamber during each of its contractions, thus reducing the forces acting against the heart muscle as it contracts and allowing the heart to pump more effectively.

Although the Batista Operation can extend the life of a patient who would otherwise die without a transplant, it is a highly invasive and traumatic procedure. In order to expose the heart, the chest must be opened widely by sawing the sternum in half and spreading apart the rib cage, known as a median sternotomy, producing a great deal of pain, risk of infection, and long recovery time. For elderly or extremely ill patients, the trauma produced by the operation could contribute significantly to the mortality and morbidity associated with the procedure.

Moreover, the Batista Operation has typically been performed while the heart is beating, causing a great deal of blood loss through the ventricular incision, and risking the introduction of air into the bloodstream, potentially causing stroke or other neurological problems. To reduce blood loss and the risk of air embolism, the heart could be stopped and isolated from the rest of the circulatory system during the procedure by placing an external aortic cross-clamp on the ascending aorta and using conventional cardioplegia and cardiopulmonary bypass. However, because such cross-clamps crush the walls of the aorta together in order to occlude the vessel, cross-clamps may produce the added risk of releasing calcific particles from the inner walls of the aorta, which may embolize in the bloodstream and produce neurological events such as stroke. Moreover, the risk remains that air will become trapped in the ventricle after it has been closed, allowing the air to migrate to the brain as soon as the cross-clamp is removed. Conventional cross-clamps also require a large opening in the chest in order to gain access to the aorta, hindering any effort to reduce the trauma associated with the procedure.

What are needed, therefore, are devices and techniques for the surgical treatment of CHF which are less invasive and less risky than the Batista Operation, but which produce the benefits associated with reducing the volume of the left ventricle. The devices and techniques should facilitate the identification of an appropriate section of the left ventricular wall, excision or other reshaping of the section, and, if the section is removed, closure of the left ventricle, without requiring a gross thoracotomy or median sternotomy. If the left ventricle is opened, the devices and techniques should allow the patient to be placed on cardiopulmonary bypass and the heart to be arrested and isolated from the circulatory system without the need for an external aortic cross-clamp. Further, the devices and techniques should minimize that risk that either air and other emboli will be produced by the procedure.

SUMMARY OF THE INVENTION

The invention provides devices and methods for treating CHF, as well as other diseases resulting in an enlarged heart, that not only significantly reduce the pain and trauma to the patient, but that may reduce the risk of infection and the risk of neurological events associated with the Batista Operation. The invention facilitates the reduction of left ventricular volume by removing a section of the heart wall or otherwise reshaping the ventricle without requiring a median sternotomy or gross thoracotomy. The invention further allows the procedure to be performed on cardiopulmonary bypass with the heart isolated and arrested, yet without the gross thoracic incision required by, or the risk of embolism produced by, conventional aortic cross-clamps. Moreover, the invention may significantly reduce the risk that air will be introduced into the bloodstream and embolized to the brain during or after the procedure.

In a first embodiment, the invention provides a method of reshaping a patient's heart, comprising the steps of:

introducing an aortic occlusion catheter through a patient's peripheral artery, the aortic occlusion catheter having an occluding member movable from a collapsed position to an expanded position;

positioning the occluding member in the patient's ascending aorta;

moving the occluding member from the collapsed shape to the expanded shape after the positioning step;

introducing cardioplegic fluid into the patient's coronary blood vessels to arrest the patient's heart;

maintaining circulation of oxygenated blood through the patient's arterial system; and reshaping an outer wall of the patient's heart while the heart is arrested so as to reduce the transverse dimension of the left ventricle.

The ascending aorta is preferably occluded by means of an occlusion balloon attached to the distal end of an elongated catheter positioned transluminally in the aorta from a femoral, subclavian, or other appropriate peripheral artery. Cardioplegic fluid may then be delivered upstream of the occlusion balloon through a lumen in that catheter, and/or delivered in a retrograde manner through a separate catheter placed transluminally into the coronary sinus from a peripheral vein. While the heart is arrested, circulation of oxygenated blood is maintained preferably by peripheral extraporeal cardiopulmonary bypass (CPB), wherein blood is removed from a peripheral vein via a venous drainage catheter, filtered, oxygenated, and returned to a peripheral artery through an arterial return catheter.

By obviating the need for an aortic cross-clamp, the need for the median sternotomy through which such a cross-clamp is placed is also eliminated. The left ventricle may then be reshaped and volumetrically reduced using thoracoscopic instruments positioned through small incisions, punctures or ports located in the intercostal spaces between the ribs.

The invention further provides a method of reshaping a patient's heart comprising the steps of:

introducing a tissue attaching device into the patient's chest;

engaging a first location on a wall of the left ventricle with the tissue attaching device; and manipulating the tissue attaching device to attach the first location to a second location on a wall of the heart so as to reduce the transverse dimension of the left ventricle, the user's hands remaining outside the patient's chest when manipulating the tissue attaching device.

In some embodiments, a section of the left ventricular wall is excised with a cutting device, then the left ventricle is closed using sutures, staples or other means for wound approximation and closure, each applied using thoracoscopic instruments with the user's hands maintained generally outside of the chest. In other embodiments, a section of the left ventricular wall is gathered together or pursed outwardly or inwardly to produce one or more folds or pleats in the wall. These folds or pleats are then thoracoscopically sutured, stapled or otherwise fastened permanently in place to reduce the transverse dimension of the left ventricle.

In the method of the invention, the left ventricular wall may be approached in several different ways. In one approach, one or more small incisions, punctures, trocar sleeves, tissue retractors or other type of ports are placed in intercostal spaces in the left anterior and/or lateral side of the chest, preferably between the third and seventh intercostal spaces. This permits direct access to the outer wall of the left ventricle on the lateral and posterior sides of the heart, usually with minor retraction of the apex of the heart anteriorly using thoracoscopic graspers or other retraction instruments. The heart may then be viewed directly through an intercostal port, or by means of a thoracoscope positioned through an intercostal port to permit either direct or video-based viewing of the heart.

In a second approach, ports are placed are in the right lateral side of the chest between the third and seventh intercostal spaces. Approaching the heart from the right, an incision is then made in the left atrium on the posterior side of the heart, and the incision retracted to expose the mitral valve. The mitral valve apparatus is excised from the heart, providing access into the interior of the left ventricle through the mitral valve annulus. A thoracoscopic scissors or knife is then used to excise a portion of the left ventricular wall from the inside of the chamber, either under direct vision from a port in the right side of the chest, or under video-based vision using a thoracoscope positioned through a port into the heart. The procedure may be viewed from outside of the heart as well by placing a thoracoscope through a port in the left lateral or anterior side of the chest. The left ventricular wall may then be closed using sutures, staples, or other means applied with an instrument introduced through the mitral annulus from the right chest, or through a port placed in the left lateral or anterior side of the chest as described above.

In still other embodiments, a restrictive girdle or band is placed around the outside of the heart to restrict the left ventricle to the desired diameter or volume. The band or girdle is preferably elastic so as to expand and contract with the heart as it pumps. Preferably, the girdle or band is applied to the heart using specialized thoracoscopic instruments placed through intercostal spaces in the rib cage while generally maintaining the user's hands outside the chest, thereby eliminating the need for a gross thoracotomy.

Because the chest is not grossly opened, the heart is isolated from the rest of the circulatory system, and in some embodiments, even the ventricle itself is not opened, the methods of the invention may reduce the risk that air will pass through the ventricular incision and into the bloodstream. To reduce this risk even further, the invention also allows the chest to be flooded with carbon dioxide or other suitable gas during the procedure to maintain the chest cavity free of air. A tube may be placed through one of the intercostal ports and gas delivered through the tube into the chest at a pressure suitable to ensure that air cannot enter the chest cavity. Additionally, trocar sleeves or tubular ports may be used which have internal seals like those used for gaseous insufflation in laparoscopic procedures, thereby preventing the unwanted introduction of air into the chest. Further, where some risk of air embolism is present due to the opening of the left ventricle, following closure the left ventricle and aorta may be flushed with saline and then vented through a lumen in the aortic occlusion catheter while maintaining aortic occlusion, thereby removing any trapped air that may be present.

The nature and advantages of the invention will become more apparent in the following detailed description, taken in conjunction with the accompanying drawings.

BRIEF DESCRIPTION OF THE DRAWINGS

FIG. 8A is a side view of a tissue gathering device according to the invention.

FIG. 8B is a top view of the distal end of the tissue gathering device of FIG. 8A.

FIG. 9A is a cross-section of a portion of the left ventricle illustrating the use of the tissue gathering device of FIG. 8A according to the method of the invention.

DESCRIPTION OF THE SPECIFIC EMBODIMENTS

Figure 1:
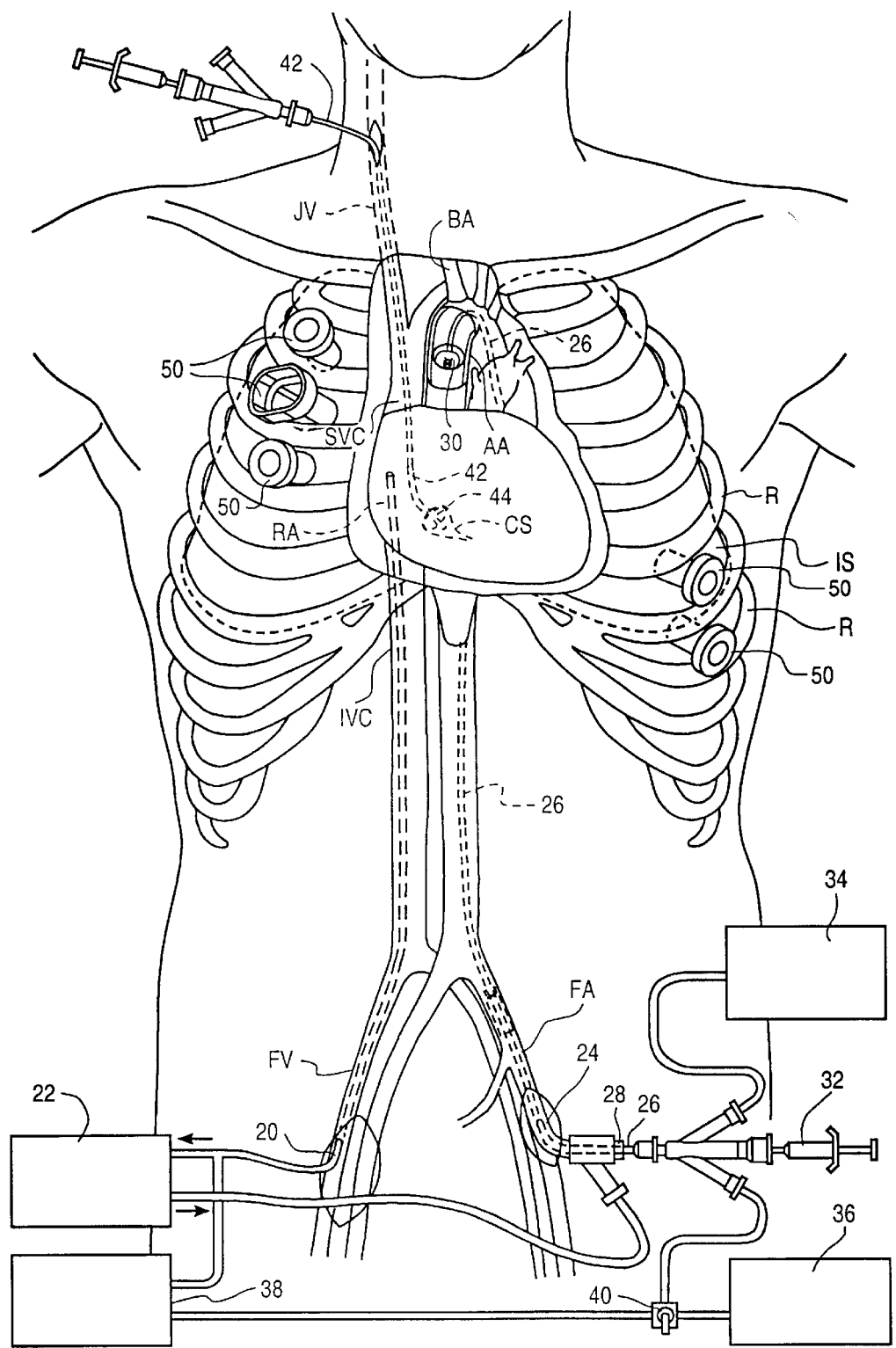
FIG. 1 is an anterior view of a patient's torso schematically illustrating the use of an endovascular cardiopulmonary bypass system according to the invention.

Referring to FIG. 1, an endovascular cardiopulmonary bypass (CPB) system useful in the method of the invention is illustrated as it is used in a patient. Additional aspects of such endovascular CPB systems suitable for use in the methods of the invention are described in the following patent applications, which are incorporated herein by reference: Ser. No. 08/282,192, filed Jul. 28, 1994, now U.S. Pat. No. 5,584,803, Ser. No. 08/612,341, filed Mar. 7, 1996, and Ser. No. 08/486,216, filed Jun. 7, 1995, now U.S. Pat. No. 5,766,151. The system includes a venous drainage cannula 20 placed into a femoral vein FV (or other suitable peripheral vein) and preferably having sufficient length to extend into the inferior vena cava IVC, the right atrium RA or the superior vena cava SVC. Venous drainage cannula 20 is connected to an extracorporeal CPB system 22, which filters and oxygenates the blood withdrawn from the patient. The system further includes an arterial return cannula 24 placed into a femoral artery FA (or other peripheral artery such as the subdlavian) through which CPB system 22 pumps oxygenated blood into the arterial system. Arterial return cannula 24, venous drainage cannula 20 and CPB system 22 are configured to provide full cardiopulmonary bypass with the patient's heart arrested.

The endovascular CPB system further includes an aortic occlusion catheter 26 that is positioned into femoral artery FA through a port 28 at the proximal end of arterial return cannula 24. Port 28 has a hemostatic seal (not shown) to prevent blood loss when occlusion catheter 26 is positioned through the port. Occlusion catheter 26 has an occlusion balloon 30 at its distal end and a length sufficient to allow occlusion balloon 30 to be positioned in the ascending aorta AA, usually at least about 80 cm. Occlusion catheter 26 preferably has at least three lumens, including an inflation lumen in communication with the interior of balloon 30 for delivery of an inflation fluid from a syringe 32 or other inflation device. A pressure lumen is also provided which communicates with a pressure port in the catheter distal to balloon 30, allowing pressure to be monitored by means of a pressure measuring device 34. Occlusion catheter 26 further includes a main lumen in communication with an additional port distal to balloon 30 to allow delivery of cardioplegic fluid from a cardioplegic fluid source 36 and to facilitate venting the aortic root by means of a suction pump 38. A two-way valve 40 permits selecting between cardioplegic fluid delivery or aortic root venting via the main lumen.

An optional component of the endovascular CPB system is a coronary sinus catheter 42 positioned translauminally into the coronary sinus CS via the internal jugular vein JV in the neck, the superior vena cava SVC, and right atrium RA. Coronary sinus catheter 42 permits retrograde delivery of cardioplegic fluid in conjunction with or instead of antegrade delivery through aortic occlusion catheter 26. The distal end of catheter 42 includes a balloon 44 configured to occlude the coronary sinus CS. Sinus catheter 42 has at least two lumens, including an inflation lumen in communication with balloon 44, and a delivery lumen in communication with a port distal to balloon 44 for delivering cardioplegic fluid into coronary sinus CS. A third lumen may optionally be provided for pressure measurement through a port distal to balloon 44.

As an additional option, an endovascular venting catheter may be introduced into a vein in the neck and advanced through the superior vena cava, the right atrium, the right ventricle and into the pulmonary artery for venting blood from the heart, as described in co-pending application Ser. No. 08/415,238, filed Mar. 30, 1995, which is incorporated herein by reference.

In use, with venous drainage cannula 20 and arterial return cannula 24 in place and blood circulating through extracorporeal CPB system 22, aortic occlusion catheter 26 is inserted through arterial return cannula 24 and slidably advanced toward the heart until occlusion balloon 30 is in the ascending aorta AA. Balloon 30 is then inflated to fully occlude the aortic lumen between the coronary ostia (not shown) and the brachiocephalic artery BA. Cardioplegic fluid, usually consisting of a cold potassium chloride solution mixed with oxygenated blood, is then delivered into the ascending aorta through the main lumen of occlusion catheter 26, from which it flows into coronary arteries and perfuses the myocardium, stopping cardiac contractions. If coronary sinus catheter 42 is utilized, balloon 44 may be inflated and cardioplegic fluid delivered into the coronary sinus CS, from which it flows through the coronary veins to perfuse the myocardium. Between periodic infusions of cardioplegic fluid, valve 40 is switched to allow the aortic root to be vented of fluid via occlusion catheter 26. Aortic root pressure may be continuously monitored using pressure measurement device 34.

Prior to arresting the heart, it may be desirable to perform a number of surgical steps in the operation up to the point of actually cutting into the myocardium so as to minimize the time for which the heart is stopped. A number of surgical ports 50, usually between about one and six, are placed in intercostal spaces IS between the ribs R. These ports may be simple plastic tubes having flanges at their proximal ends to prevent passage entirely into the chest and having sufficient rigidity to retract intercostal tissue so as to form an opening. Trocar sleeves or small bladed rib retractors may also be used. A soft tissue retractor that may be particularly useful in the method of the invention is described in application Ser. No. 08/610,619, filed Mar. 4, 1996, now U.S. Pat. No. 5,810,721, which is incorporated herein by reference. In some cases, instruments may be placed directly through incisions or punctures between the ribs without any type of retraction. In any case, all of the aforementioned means of access into the chest will be referred to herein as ports.

Ports 50 may be positioned in any of several regions of the chest, depending upon the desired approach to heart. For approaching the left ventricle on the posterior side of the heart, ports 50 are preferably placed in the fourth, fifth, sixth or seventh intercostal spaces on the left anterior and/or left lateral side of the patient's chest. For approaching the left ventricle from within the heart via the left atrium and the mitral valve, ports 50 are placed in the right lateral side of the chest in the second, third, fourth, fifth, or sixth intercostal spaces. Of course, it will be understood that the exact location of ports 50 will depend upon the location of the surgical site on the heart, individual patient anatomy, and surgeon preference.

Figure 2:
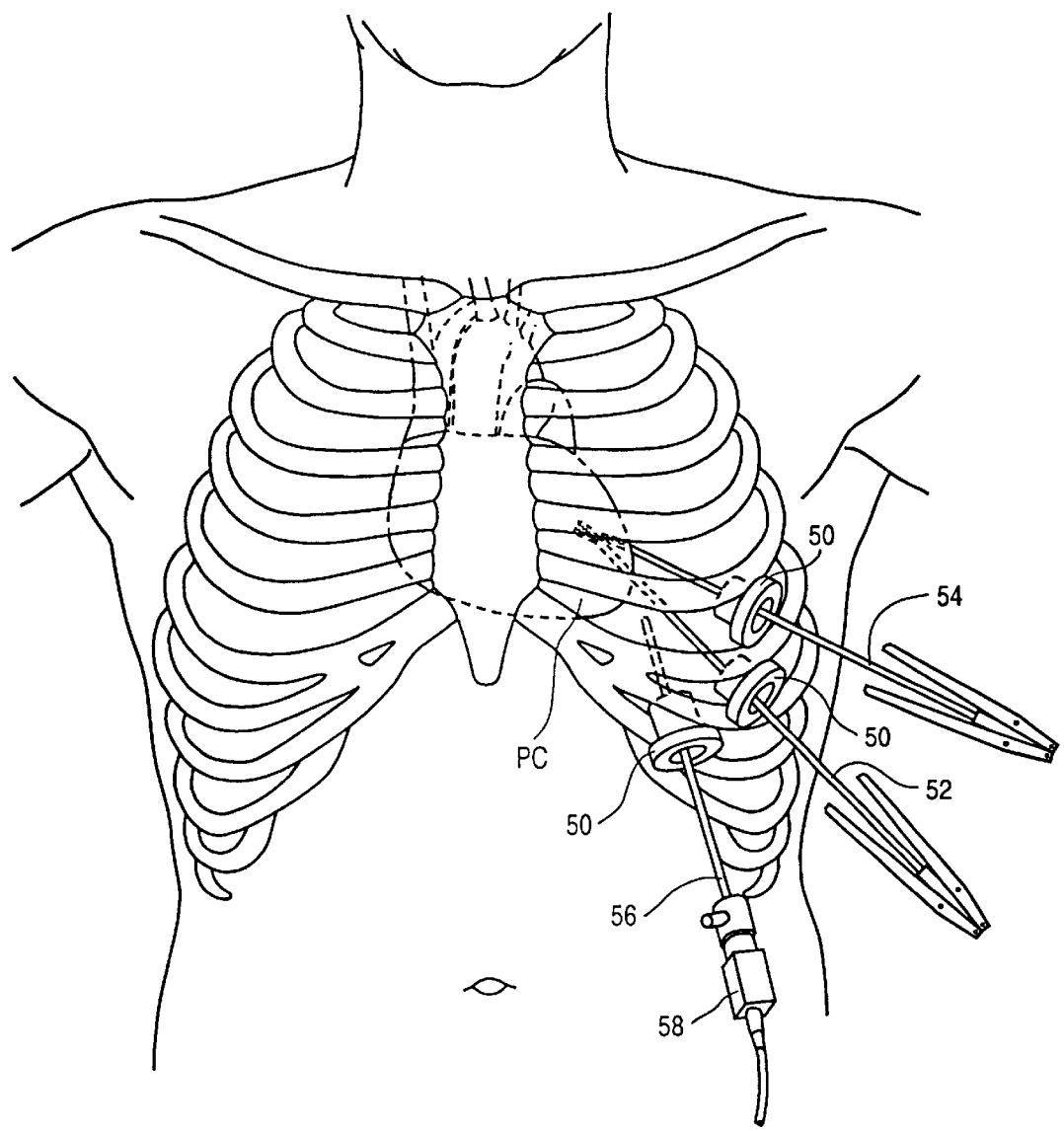
FIG. 2 is an anterior view of a patient's chest illustrating the placement of intercostal ports and thoracoscopic instruments according to the invention.

One or both of the patient's lungs may have to be partially or fully collapsed during the procedure in order to gain access to the heart. With the lungs collapsed, the pericardium PC is incised, as illustrated in FIG. 2, using thoracoscopic scissors 52, an electrocautery probe or other appropriate cutting devices, along with graspers 54 or other retraction devices, inserted through ports 50. Suitable instruments are described in U.S. Pat. No. 5,501,698, which is incorporated herein by reference. A thoracoscope 56 is inserted through one of ports 50 to facilitate visualization. Thoracoscope 56 includes a camera 58 which produces a video image of the interior of the chest that can be viewed on a video monitor (not shown). Various conventional thoracoscopes may be used, including the articulating Welch-Allyn DistalView 360 (Welch-Allyn, Skaneateles Falls, N.Y.), or a 30□ angled endoscope available from Olympus Optical (Lake Success, N.Y.). The surgeon may also look directly into the chest through ports 50, assisted by illumination of the chest by means of a light probe inserted through a port. The pericardium is opened or removed from around the left ventricle to expose the surgical site.

Figure 3:
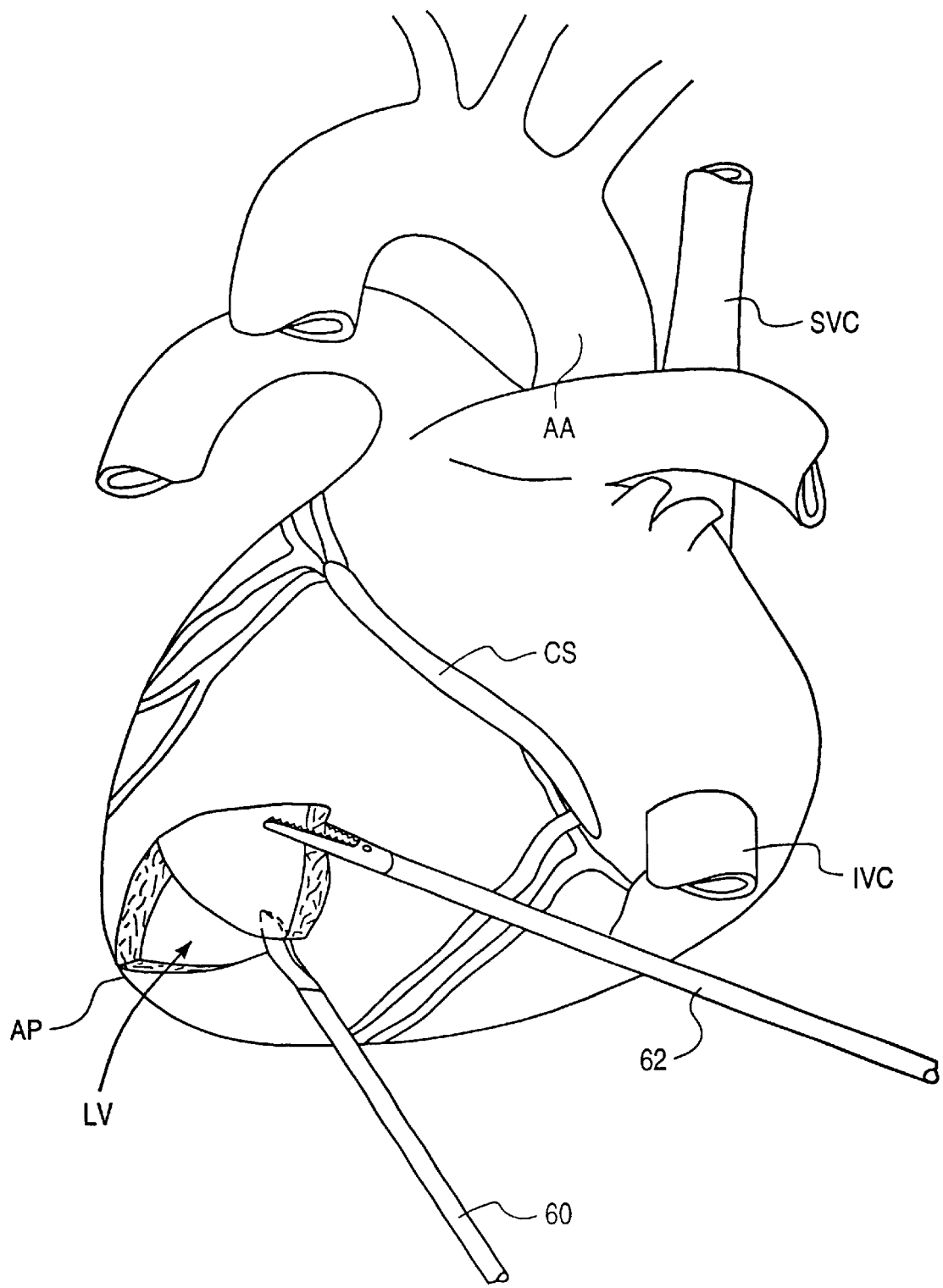
FIGS. 3–5 are posterior views of a patient's heart illustrating the removal of a section of the left ventricle and closure of the left ventricular wall according to the invention.
Figure 4:
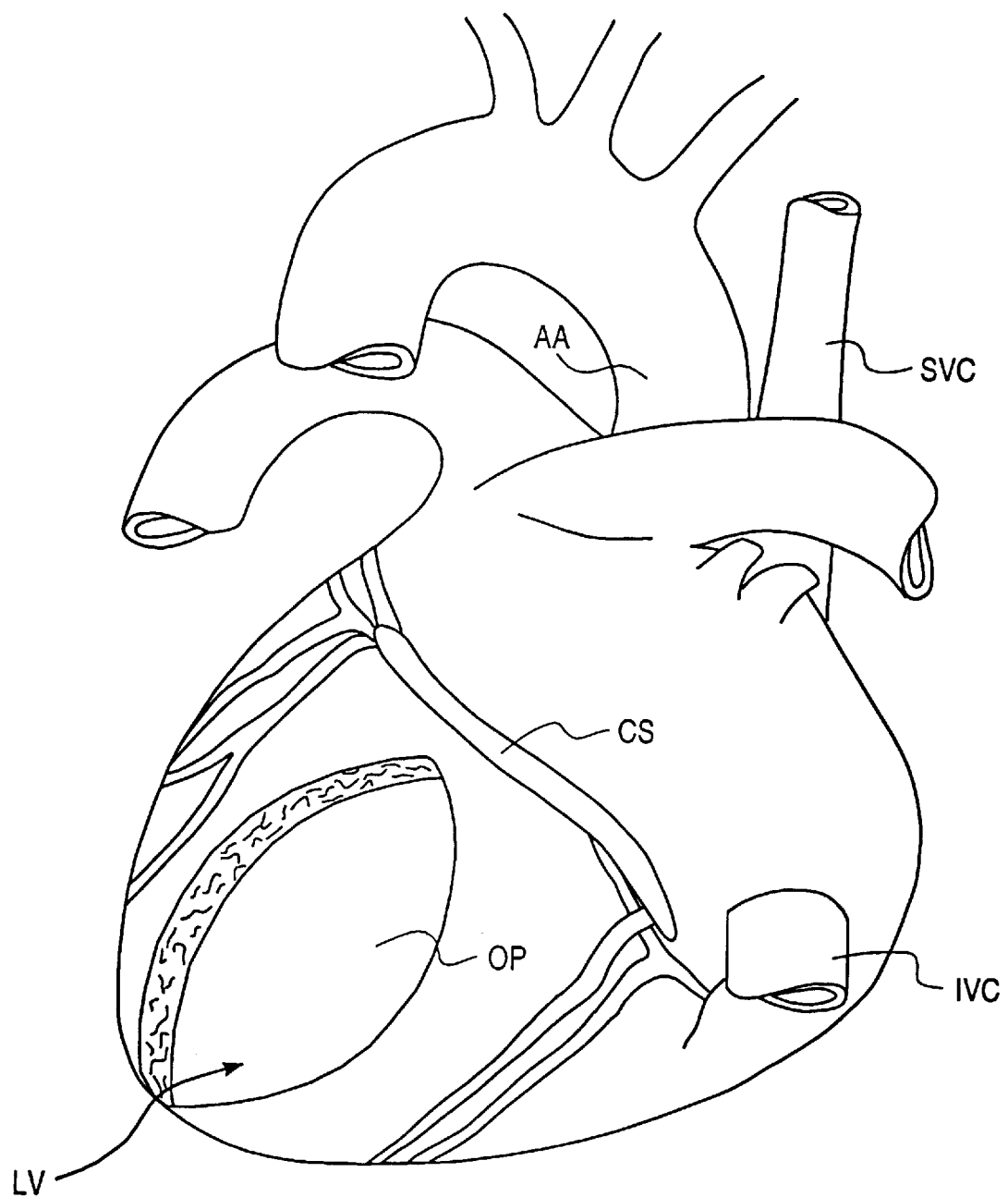

In a first embodiment of the ventricular volume reduction procedure of the invention, a portion of an outer wall of the left ventricle is removed and the wall then re-closed so as to reduce the traverse dimension and volume of the ventricular chamber. Referring to FIG. 3, a posterior view of the heart, with the patient's heart arrested and circulation maintained by CPB system 22, a cutting device such as a knife 60 along with thoracoscopic graspers 62 are inserted though ports 50 and used to excise the desired portion of the ventricular wall. During the procedure some retraction of the heart may be required, by for example, grasping the apex of the heart with graspers 62 and moving the apex anteriorly so as to expose the posterior aspect of the left ventricle. Using knife 60, a stab wound is made near the apex AP of the heart and an incision extended superiorly toward the left atrium in an arc bowing outwardly toward the left side of the heart. A second incision is made from the apex in an opposing arc bowing outwardly toward the right side of the heart and intersecting the first incision near the coronary sinus CS, allowing a football-shaped section of myocardial tissue to be removed. This leaves an opening OP in the left ventricular wall as illustrated in FIG. 4.

Opening OP is then sutured closed using thoracoscopic needle drivers 64 to drive curved needle 66 and suture 68 through ventricular wall VW and using graspers 62 to assist in approximating the opposing edges of the opening. Usually a relatively coarse running stitch is placed in the wall to draw opening OP closed, and a finer running stitch is then applied to ensure the wound is hemostatically sealed.

The exact location and amount of tissue removed from the left ventricular wall will vary according to the type and severity of disease and other factors. The effectiveness of the heart in pumping blood will generally be increased by reducing the transverse dimension of the left ventricle so as to reduce the overall volume of the chamber. This allows less blood to flow into the left ventricle before each contraction, thereby reducing the outward force of the blood against the ventricle when it contracts. Preferably, a sufficiently large section of the ventricular wall will be removed to reduce the ventricle to having a transverse dimension (generally perpendicular to the interventricular septum) on the order of 4 to 7 cm.

Generally, opening OP in the left ventricular wall will be formed between the anterior and posterior papillary muscles, avoiding unnecessary damage to the mitral valve apparatus. In some cases, however, the mitral valve apparatus is damaged or removed during the procedure, requiring replacement or repair of the valve following removal of the ventricular wall section. This may be accomplished by introducing an annuloplasty ring or prosthetic valve into the heart through ports 50 and opening OP and securing the prosthesis at the mitral valve position using thoracoscopic instruments introduced through ports 50. Alternatively, the mitral valve may be replaced via ports in the right lateral side of the chest by entering the left atrium, using the techniques described in co-pending application Ser. No. 08/465,383, filed Jun. 5, 1995, now U.S. Pat. No. 5,682,906, which is hereby incorporated herein by reference.

Following closure of the left ventricular wall, ports 50 are removed and thoracic incisions are closed. Cardioplegic fluid infusions are discontinued and the aortic root is vented through occlusion catheter 26 to remove any air or other particles which may be present in the heart or aorta. If desired, saline may be delivered through the main lumen of the occlusion catheter into the aortic root, or a small catheter may be advanced through the occlusion catheter and into the left atrium through the aortic valve to deliver saline into the left ventricle. The heart may be compressed using thoracoscopic probes to urge air out of the left ventricle. The saline is then vented through occlusion catheter 26 to remove air and other emboli. In order to restart heart contractions, occlusion balloon 30 on aortic occlusion catheter 26 is deflated to allow blood from arterial return cannula 24 to reach the coronary ostia. If cardiac contractions do not resume spontaneously, an electric shock may be delivered to the heart using thoracoscopic or external defibrillation paddles. When the heart is in sinus rhythm, the patient is weaned from cardiopulmonary bypass, vascular punctures are closed, and the patient recovered from general anesthesia.

Because the left ventricle is opened during the procedure, it will be desirable to keep air out of the chest cavity to the maximum extent until the ventricle is closed. For this purpose, ports 50 may be provided with gaseous seals like those used in laparoscopic trocar sleeves to maintain an air-free environment within the chest. In addition, a gas such as carbon dioxide that is not likely to embolize in the blood stream may be delivered into the chest at a sufficient rate and pressure to prevent air from entering. Other techniques for preventing air embolism are described in co-pending application Ser. No. 08/585,871, filed Jan. 12, 1996, now U.S. Pat. No. 5,849,005 which is incorporated herein by reference.

FIGS. 6A–6D are transverse cross-sections of a patient's thorax and heart illustrating additional embodiments of the method of the invention. In these embodiments, a right chest approach is used similar to that described in co-pending application Ser. No. 08/465,383, now U.S. Pat. No. 5,682,906, which has been incorporated herein by reference. That application describes techniques for opening the pericardium, forming and retracting an atrial incision, removing the mitral valve, and implanting a valve prosthesis which may be utilized in the method of the present invention.

Preferably, ports 50A are placed in the second, third, fourth, fifth, or sixth intercostal spaces in the right lateral side of the chest. Optionally, additional ports 50B may be placed in the left lateral or left anterior sides of the chest to approach the left ventricle on the posterior side of the heart, as described above with reference to FIGS. 1–2. An opening is first formed in the pericardium using thoracoscopic instruments inserted through right chest ports 50A and/or left chest ports 50B so as to expose the left atrium LA and the left ventricle LV. A thoracoscope 70 may be inserted through one of ports 50A to view the interior of the chest, or the surgeon may view the chest cavity directly by looking through ports 50A. If desired, one or more of ports 50A may be configured to provide a wider opening into the chest to allow greater maneuverability of instruments and to facilitate direct vision into the chest, such as the oval-shaped port described in application Ser. No. 08/465,383, now U.S. Pat. No. 5,682,906, or the soft tissue retractor described in application Ser. No. 08/610,619, now U.S. Pat. No. 5,810,721, referenced above. Preferably, these will not require cutting or removing the ribs, and will minimize any retraction of the ribs, although in some cases it may be desirable to retract the ribs slightly or remove a small portion of a rib to provide greater access into the chest. However, ports 50A will generally not be large enough to allow the surgeon's hands to be placed into the chest, although it may be possible to place one or more individual fingers into the chest.

The right lung is collapsed, the pericardium is opened and the patient is on CPB with the heart arrested as described above. An incision is made in the left atrium on the right lateral/posterior aspect of the heart using thoracoscopic scissors or knife inserted through a port 50A. The atrial incision is then retracted anteriorly using a thoracoscopic retractor 72. Suitable retractors are described in co-pending application Ser. No. 08/577,547, filed Dec. 22, 1995 which is hereby incorporated herein by reference.

With the atrial incision retracted in this manner, the mitral valve is exposed at a direct line of sight from a port 50A in the fourth, fifth, or sixth intercostal space in the right chest. The mitral valve leaflets may then be removed using thoracoscopic scissors so that the left ventricle LV is visible through the mitral valve annulus VA. The valve leaflets and chordae tendonae may alternatively be left intact, and a thoracoscope introduced through the valve into left ventricle LV to provide visualization within the chamber.

Figure 6A:
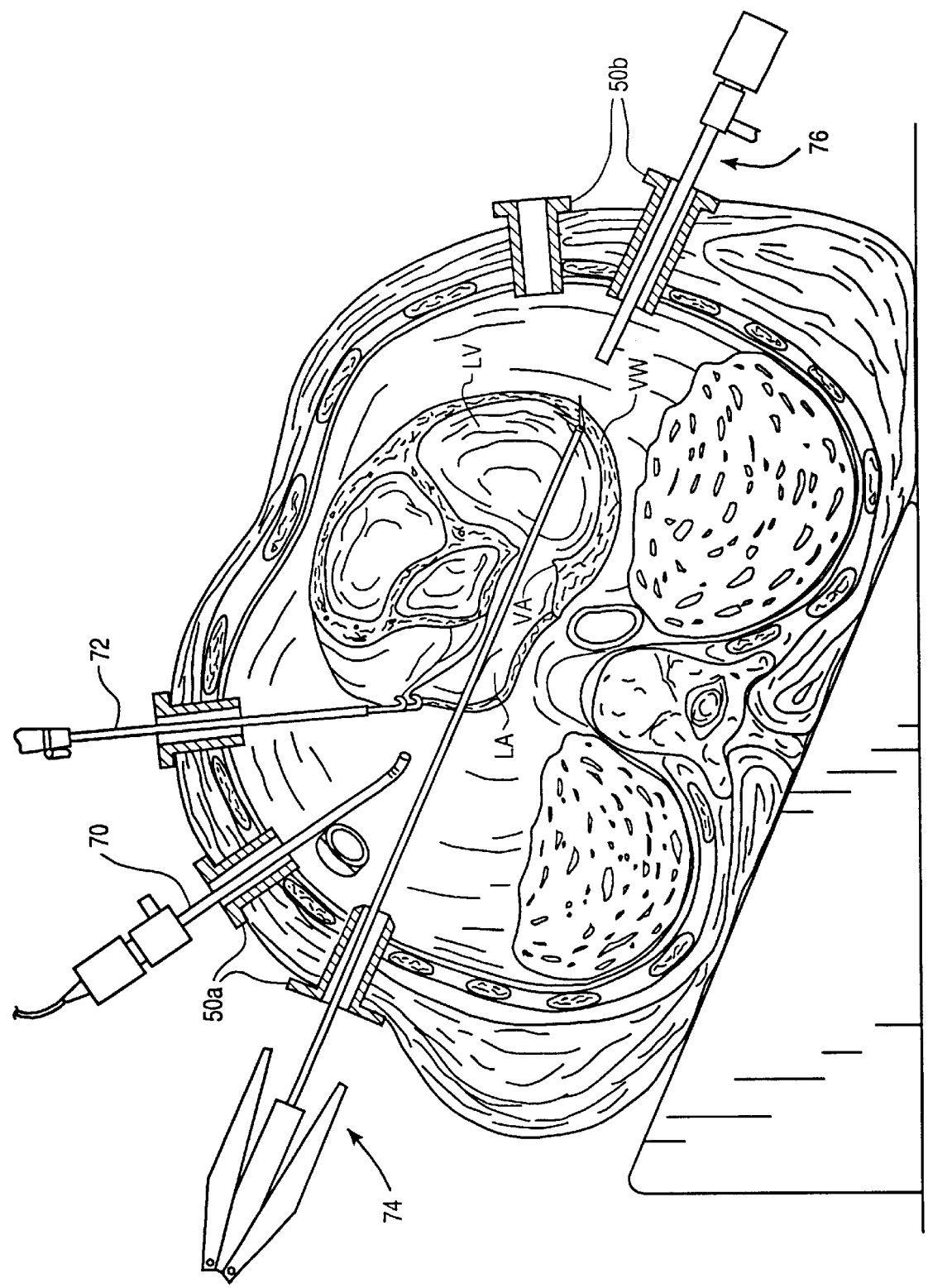
FIG. 6A is a transverse cross-section of a patient's chest illustrating an alternative approach to the left ventricle according to the invention.

In the embodiment shown in FIG. 6A, a section of the left ventricular wall VW is then removed using elongated thoracoscopic scissors 74 or other suitable cutting device introduced through a port 50A and valve annulus VA. Scissors 74 are used to excise a football-shaped section of ventricular wall tissue, preferably between the anterior and posterior papillary muscles. An additional thoracoscope 76 may be introduced through left lateral chest ports 50B with the left lung collapsed to visualize the outer wall of the left ventricle to ensure the desired section is removed without cutting into adjacent tissues.

Figure 5:
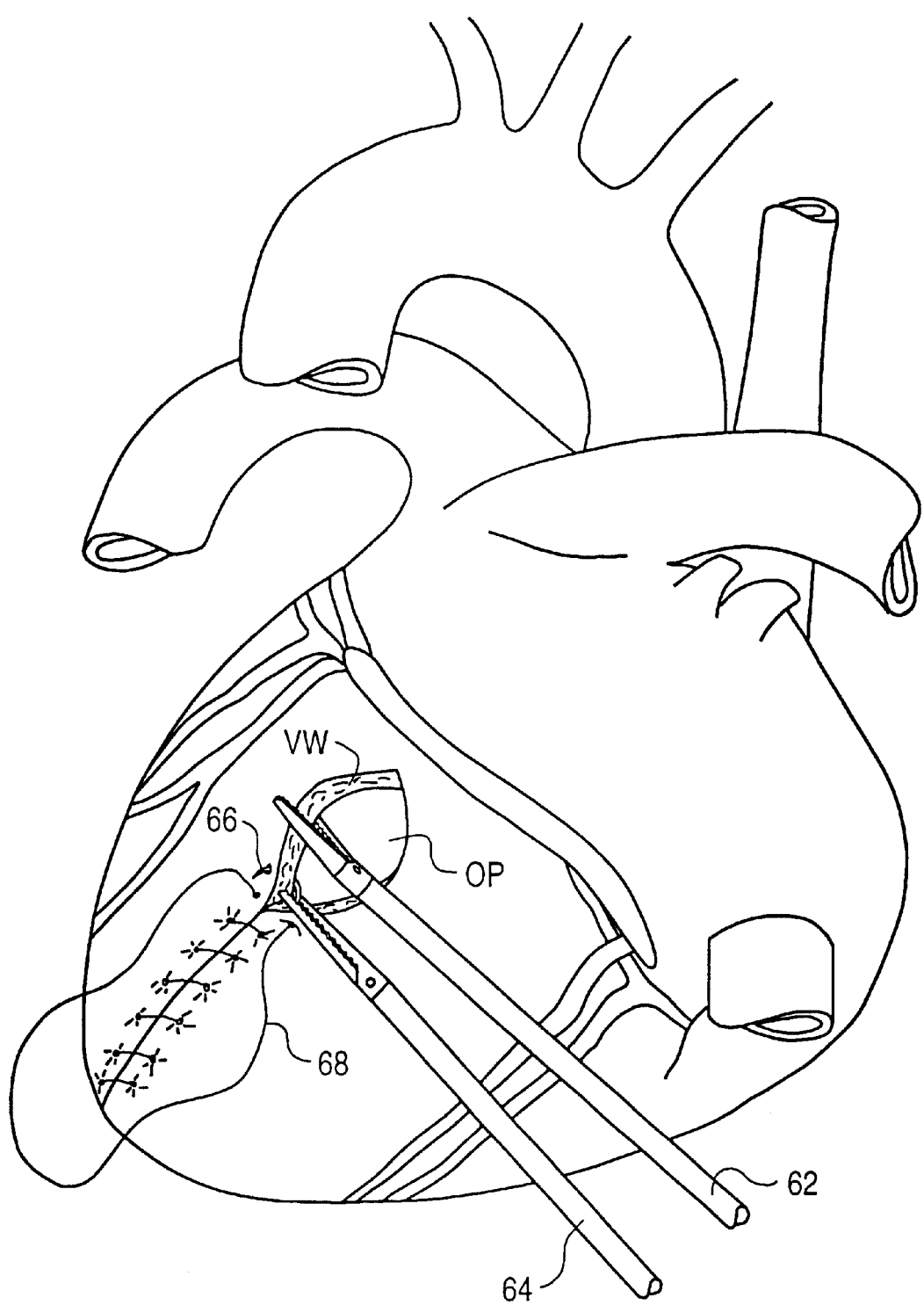

The left ventricular wall is then closed in one of two ways. Ventricular wall VW may be sutured from within the chamber with thoracoscopic needle drivers introduced through right chest ports 50A and mitral valve annulus VA, or sutured from outside the heart using needle drivers inserted through left chest ports 50B as described above in connection with FIG. 5. Advantageously, should the mitral valve require repair or replacement after the ventricular wall has been closed, excellent access is provided through right chest ports 50A to implant either a replacement valve or an annuloplasty ring, or perform any necessary surgical repair of the valve, in the manner described in co-pending application Ser. No. 08/465,383, now U.S. Pat. No. 5,682,906, already incorporated herein by reference. The left atrium is then closed. Ports 50A, 50B are removed and thoracic incisions are closed. The heart is restarted and the patient is weaned from cardiopulmonary bypass as described above.

Figure 6B:
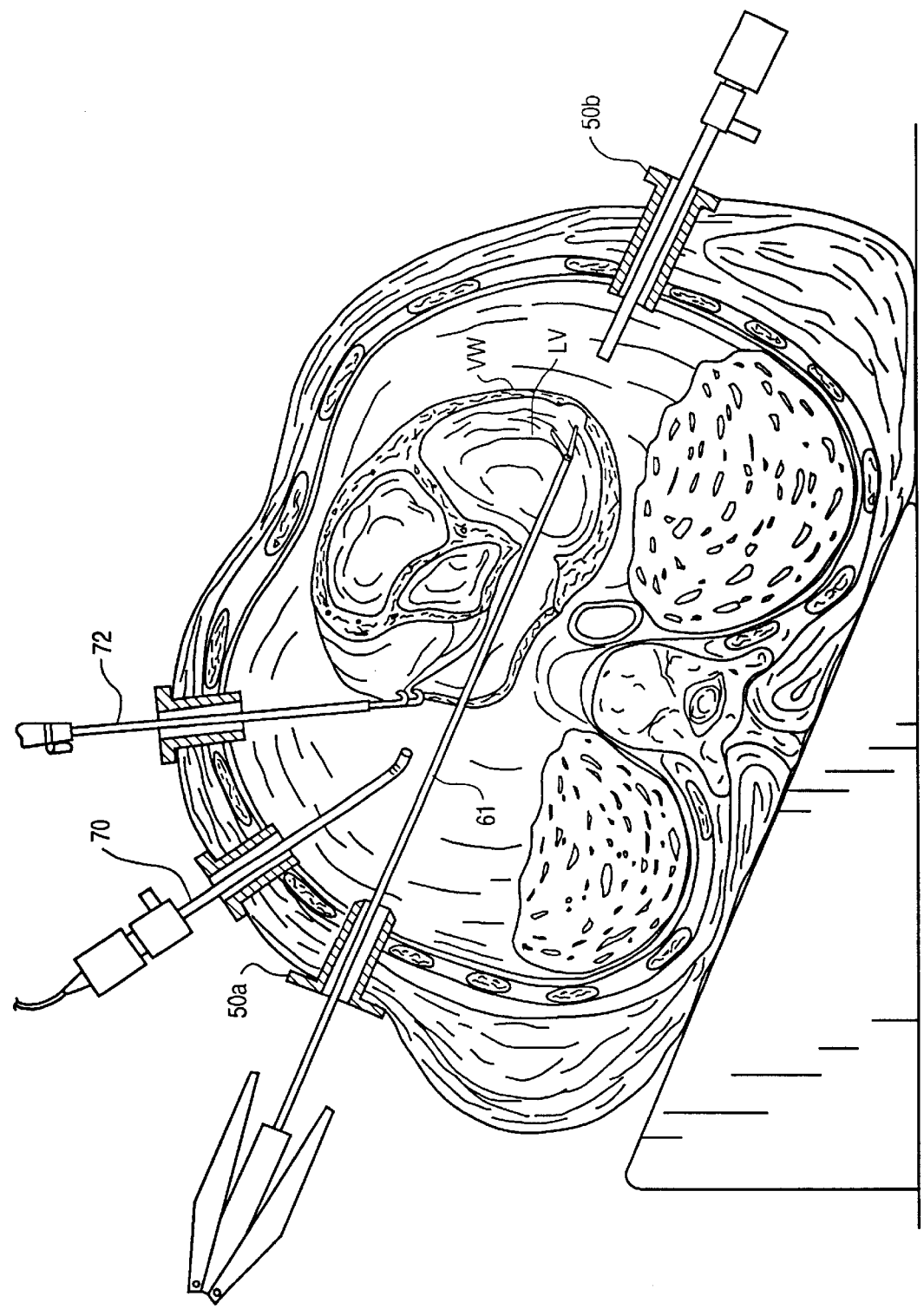
FIG. 6B is a transverse cross-section of a patient's chest illustrating an alternative method of ventricular volume reduction according to the invention.
Figure 6D:
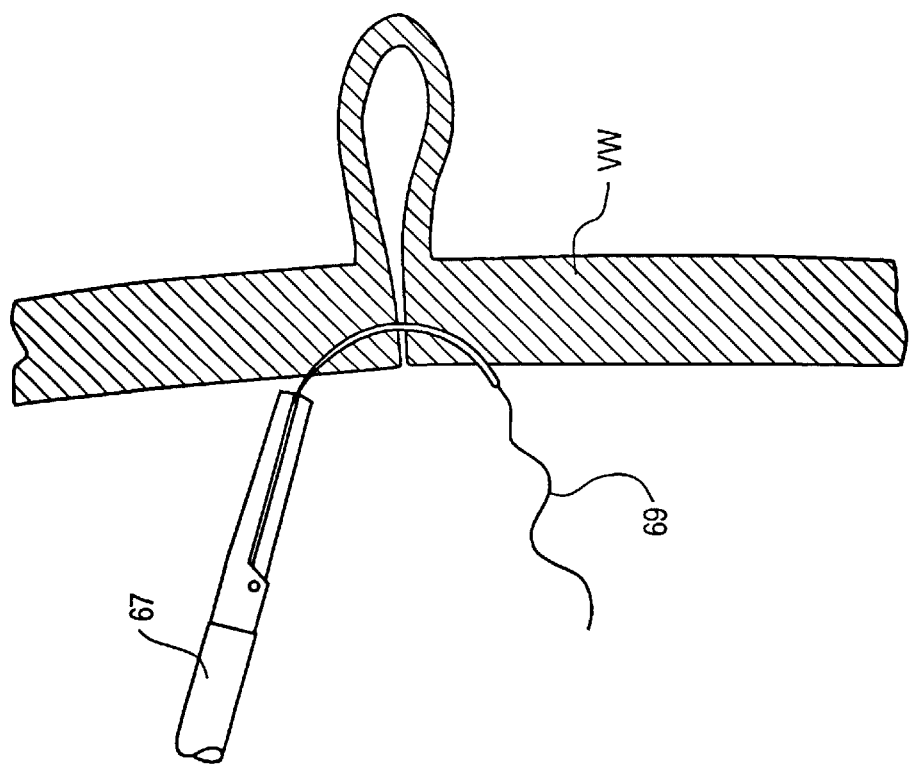
FIGS. 6C–6D are close-up cross-sections of the ventricular wall illustrating additional steps in the method of FIG. 6B.
Figure 6C:
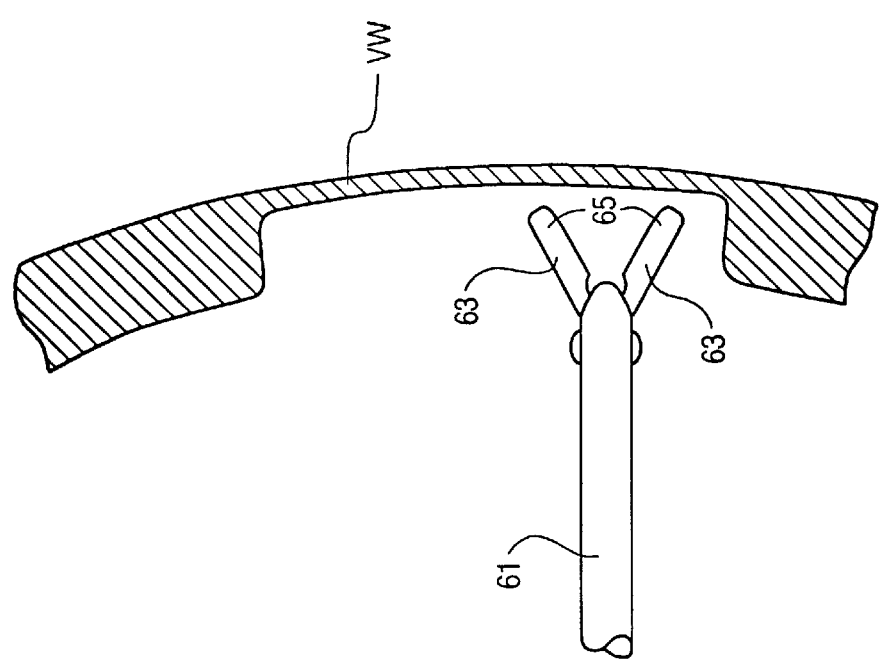

In an alternative embodiment, shown in FIGS. 6B–6D, rather than cutting entirely through the heart wall to remove a section of the wall, a section of the inner wall of the heart is removed while leaving a thin layer of the outer wall intact. For this purpose, a thoracoscopic tissue-removing instrument 61, such as an end-biting biopsy or rongeur type instrument, may be utilized which has a pair of pivotable jaws 63 with tissue-cutting cup-shaped tips 65 that interact in a shearing relationship to bite off a portion of tissue, as shown in FIG. 6C. A variety of other conventional endoscopic tissue removal instruments may also be used. In this way, a very thin section of the ventricular wall is created in the area which would otherwise be removed according to the alternative methods described above. Ventricular wall VW is then drawn together and sutured so that the thin section of the wall is pursed outward, as shown in FIG. 6D. A thoracoscopic needle driver 67 may be inserted through a right chest port 50A and through the mitral valve to apply a suture 69, or a needle driver may be inserted through a left lateral or anterior port 50B to apply sutures from the exterior of the heart. In some cases, it may be desirable to progressively draw the heart wall closer and closer together, by first drawing together only a portion of the thin-walled section and suturing it in place, then drawing together a wider portion, suturing it, and repeating the process until the entire thin-walled section has been folded together and the ventricle is of the desired dimension.

Figure 7A:
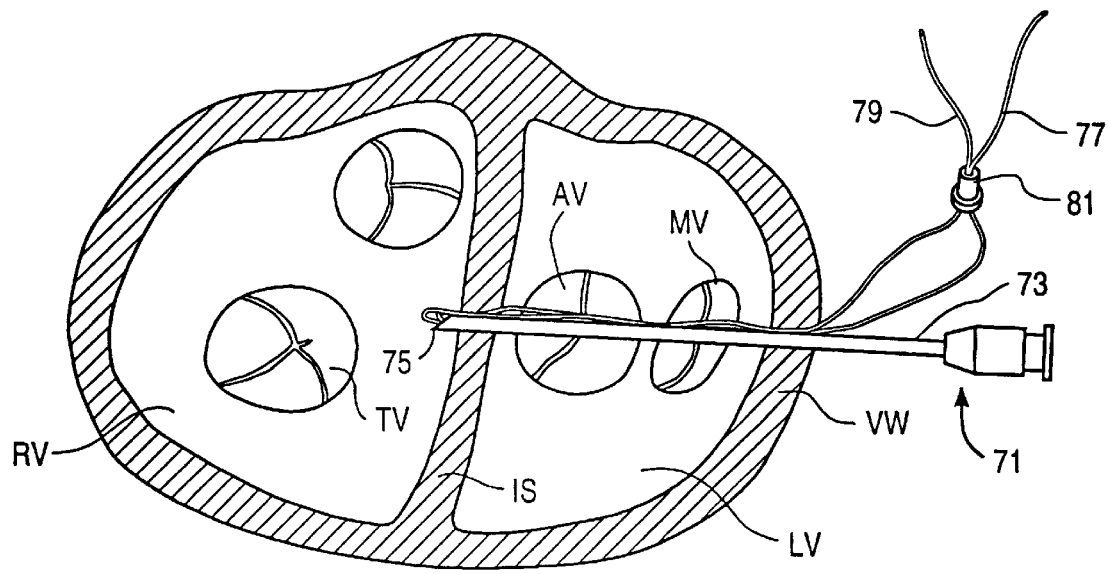
FIGS. 7A–7B are transverse cross-sections of a patient's heart before and after treatment, respectively, illustrating the bifurcation of the left ventricle according to the invention.
Figure 7B:
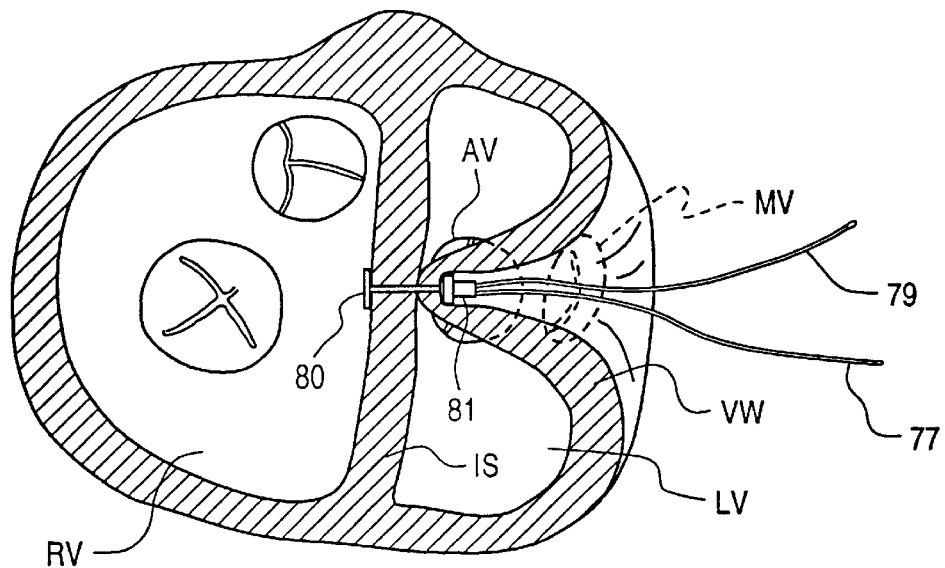
Figure 7C:
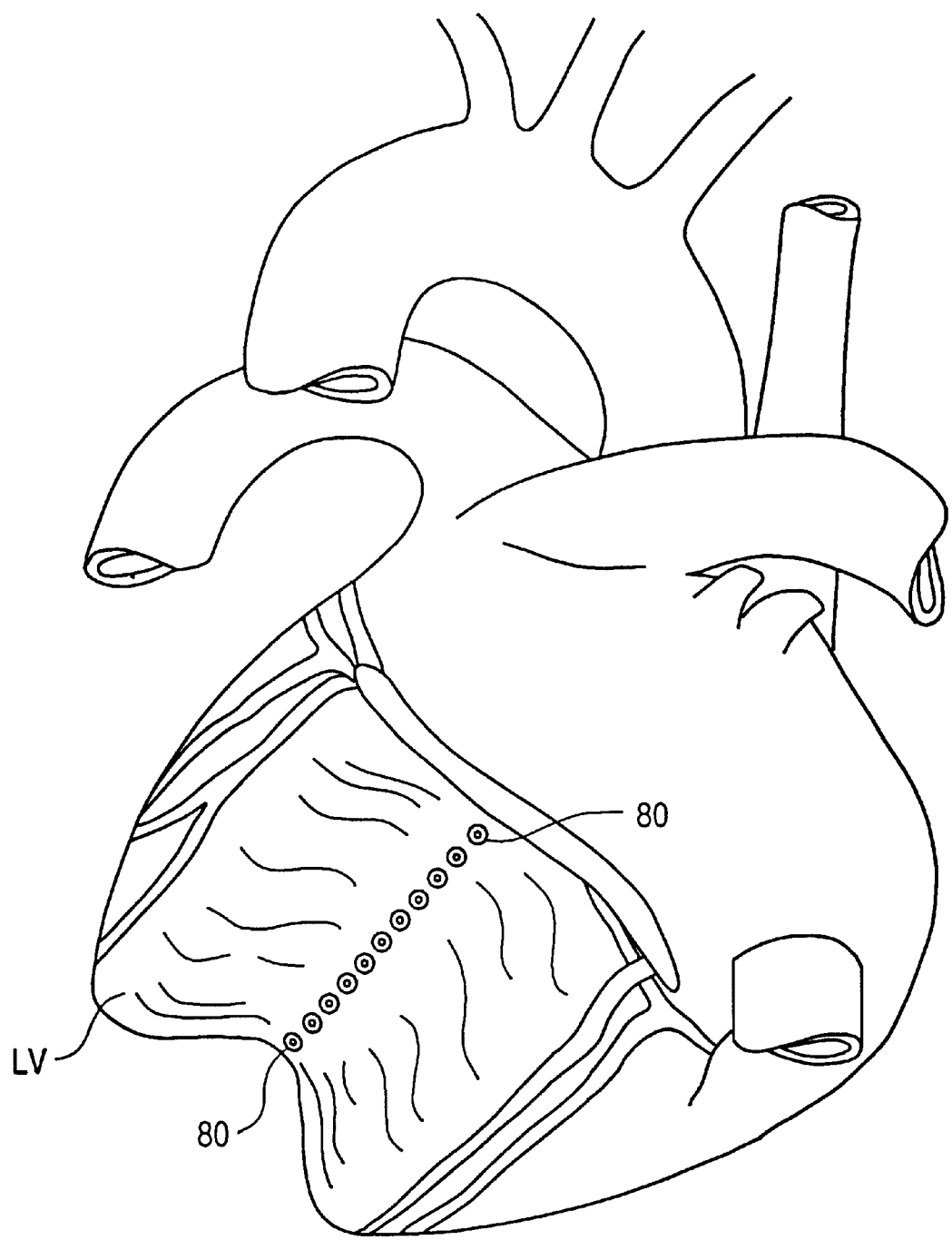
FIG. 7C is a posterior view of a patient's heart illustrating the exterior shape of the left ventricle after bifuircation as in FIG. 7B.

FIGS. 7A–7C illustrate a further embodiment of the method of the invention. In this embodiment, rather than removing a section of the left ventricle, the ventricle is reshaped by attaching a central longitudinal section of the ventricular wall VW to the interventricular septum IS. This is most readily accomplished by inserting a thoracoscopic tissue attachment device through left chest ports 50B (FIG. 2), exerting inward pressure against the left ventricular wall VW until it abuts septum IS, and securing wall VW to septum IS. The tissue attachment device comprises, in an exemplary embodiment, an insertion device 71 for applying a T-shaped fastener like that described in reissued U.S. Pat. No. Re 34,021, incorporated herein by reference. Insertion device 71 has a tubular shaft 73 with a sharpened distal end 75 used to penetrate ventricular wall VW and interventricular septum IS. A suture 77 is attached to a central portion of a fastener 80 (not shown in FIG. 7A) which is removably positioned in tubular shaft 73 during insertion. A second suture 79 is also attached to an end of fastener 80 for removal purposes, as described in the aforementioned reissue patent. Once distal end 75 has penetrated system IS, an obturator (not shown) is positioned through tubular shaft 73 so as to deploy fastener 80 into the right ventricle RV. Insertion device 71 is then removed from the heart, leaving sutures 77,79 extending through the septum IS and ventricular wall VW. A retainer 81, slidably mounted on sutures 77,79, is then advanced against ventricular wall VW to urge the ventricular wall against septum IS, as shown in FIG. 7B. A series of fasteners 80 are applied in this way along a generally vertical line extending from the apex of the heart toward the superior aspect of the heart so as to bifurcate the ventricle into two separate chambers communicating with each other and with the aortic valve AV and mitral valve MV at the superior end of the chambers. Each of the smaller chambers thus created has a smaller transverse dimension and volume than the left ventricle, and the contraction of each chamber is therefore opposed by a smaller outward force from blood present in the chamber than that to which the single larger ventricle is subject. It will be understood that a variety of tissue attachment techniques may be used instead of the T-shaped fastener illustrated, including suturing by means of a large curved needle and thoracoscopic needle drivers, or skin or fascia type staplers. A particular advantage of this technique is that it does not require the left ventricle to be opened and exposed to air, thereby eliminating the risk of air embolism resulting from the procedure. Additionally, the technique avoids any loss of blood from the ventricle, allowing it to be performed on the beating heart, without occluding the aorta, arresting the heart, or placing the patient on CPB.

A further embodiment of a method of ventricular volume reduction will now be described in connection with FIGS. 8A–8B and 9A–9B. In this embodiment, a thoracoscopic tissue gathering device is utilized, an exemplary embodiment of which is illustrated in FIGS. 8A–8B. Tissue gathering device 84 comprises an elongated tubular shaft 86 and an inner rod 88 extending slidably through shaft 86. A tissue engaging member 90 is attached to the distal end of rod 88. Tissue engaging member 90 comprises a pair of jaws 92 biased away from each other and connected at their proximal ends to rod 88. The lateral surfaces 94 of jaws 92 are engaged by the inner wall of shaft 86 such that sliding the shaft distally relative to rod 88 urges jaws 92 toward one another. A plurality of sharp points or teeth 96 extend inwardly from a distal portion of jaws 92 and are configured to penetrate the ventricular wall, as described below. Jaws 92 may be as narrow as the diameter of shaft 86 or even narrower, if desired, with only one or two opposing teeth 96, but are preferably somewhat wider as illustrated, e.g. 1–5 cm in width (transverse to shaft 86), with three or more teeth 96 on each jaw, to facilitate gathering a wide section of tissue between them. The distal transverse portion 97 of jaws 92 on which teeth 96 are disposed is preferably arcuate in shape to facilitate grasping a curved section of tissue between the jaws.

A handle 98 is attached to the proximal end of shaft 86 and includes a stationary handle member 100 having finger loops 101 and a movable handle member 102 pivotably attached to stationary handle member 100 and having thumb loop 103. The proximal end of rod 88 is attached to movable handle member 102 such that pivoting the movable handle member toward the stationary handle member pulls rod 88 proximally relative to shaft 86, thereby closing jaws 92. A locking mechanism 104 facilitates maintaining the jaws in the closed position without maintaining pressure on handle 100.

Figure 9B:
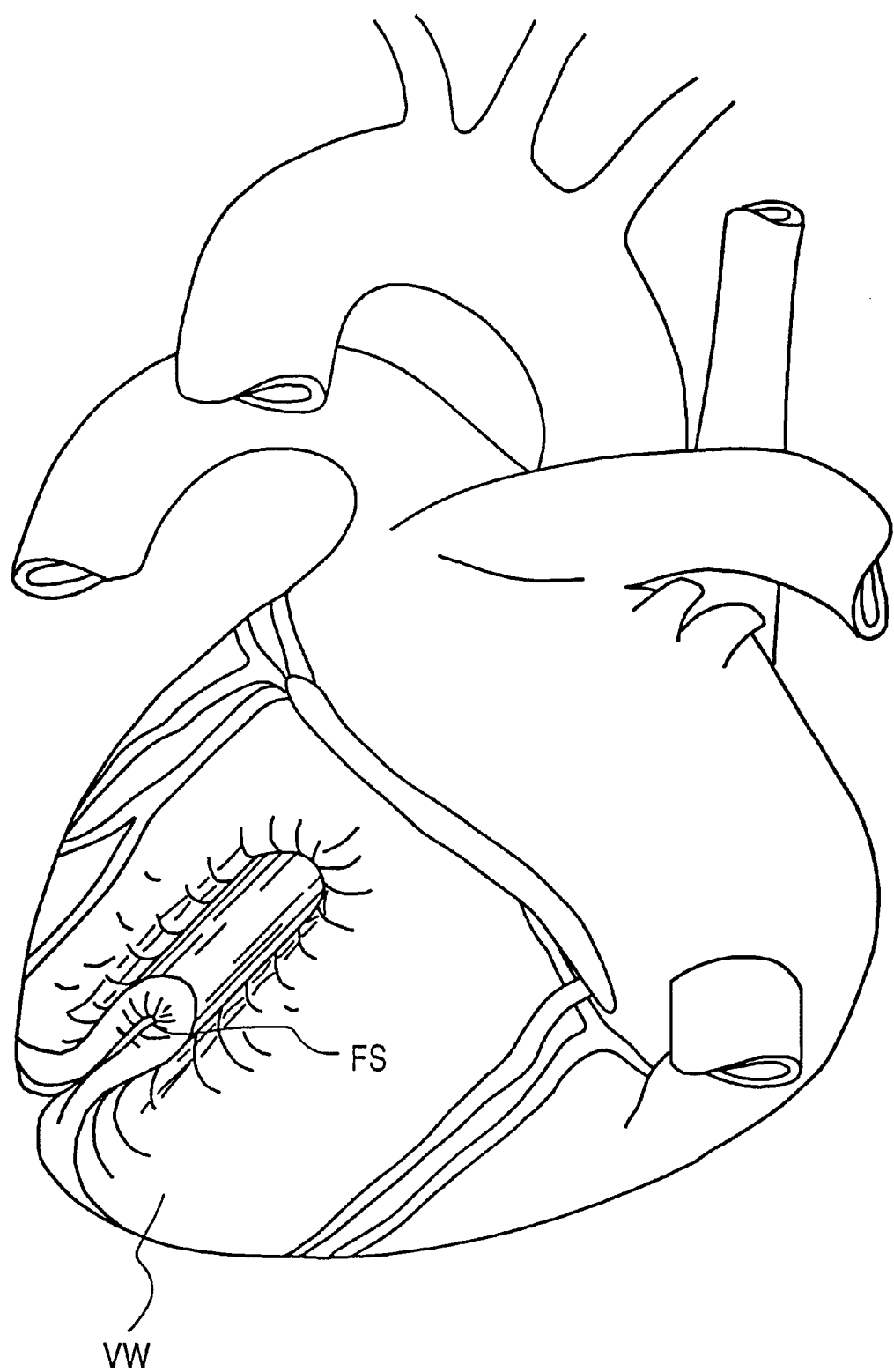
FIG. 9B is a posterior view of a patient's heart illustrating the heart after treatment using the tissue gathering device of FIG. 8A.

The use of tissue gathering device 84 in the method of the invention is illustrated in FIGS. 9A–9B. Tissue gathering device 84 is introduced through a port 50B (FIG. 2) in the left lateral or anterior side of the chest selected to allow access to the left ventricle on the posterior side of the heart near the apex. The heart may be retracted as necessary to facilitate access and visualization of the left ventricle either directly or by means of a thoracoscope. Jaws 92 are positioned in the open position against the ventricular wall VW and closed so as to gather a section of ventricular wall tissue between the jaws, as illustrated in FIG. 9A. Usually this will be an arcuate section of tissue extending from a point near the apex superiorly along the left ventricle on the posterior side of the heart. Points 96 penetrate the outer surface of the ventricular wall to facilitate grasping the wall tissue and pursing it outwardly between the jaws. Locking mechanism 104 on handle 100 may then be engaged so as to lock jaws 92 in position, thereby maintaining the gathered section of ventricular wall tissue between jaws 92.

The opposing halves of the folded section of wall tissue are then attached to one another near the base of the fold, using a large arcuate needle 108 attached to a suture 110, driven by a thoracoscopic needle driver 112 inserted through a port 50. A running stitch may be applied, or a series of individual suture loops. Alternatively, a thoracoscopic stapler, T-fastener applier, or other suitable tissue fastening device may be used. The result is shown in FIG. 9B. A large section FS of left ventricle LV has been folded outwardly and isolated from the remainder of the ventricle, thereby reducing the transverse dimension and volume of the ventricle. If desired, the outer portion of the folded section FS may be cut off and removed using a thoracoscopic scissors or knife.

Advantageously, as in the embodiment described above in reference to FIGS. 7A–7C, the left ventricle is not opened during the procedure, eliminating the risk of air embolism, and avoiding blood loss, thus allowing the procedure to be performed on a beating heart without cardiac arrest and CPB.

Figure 10:
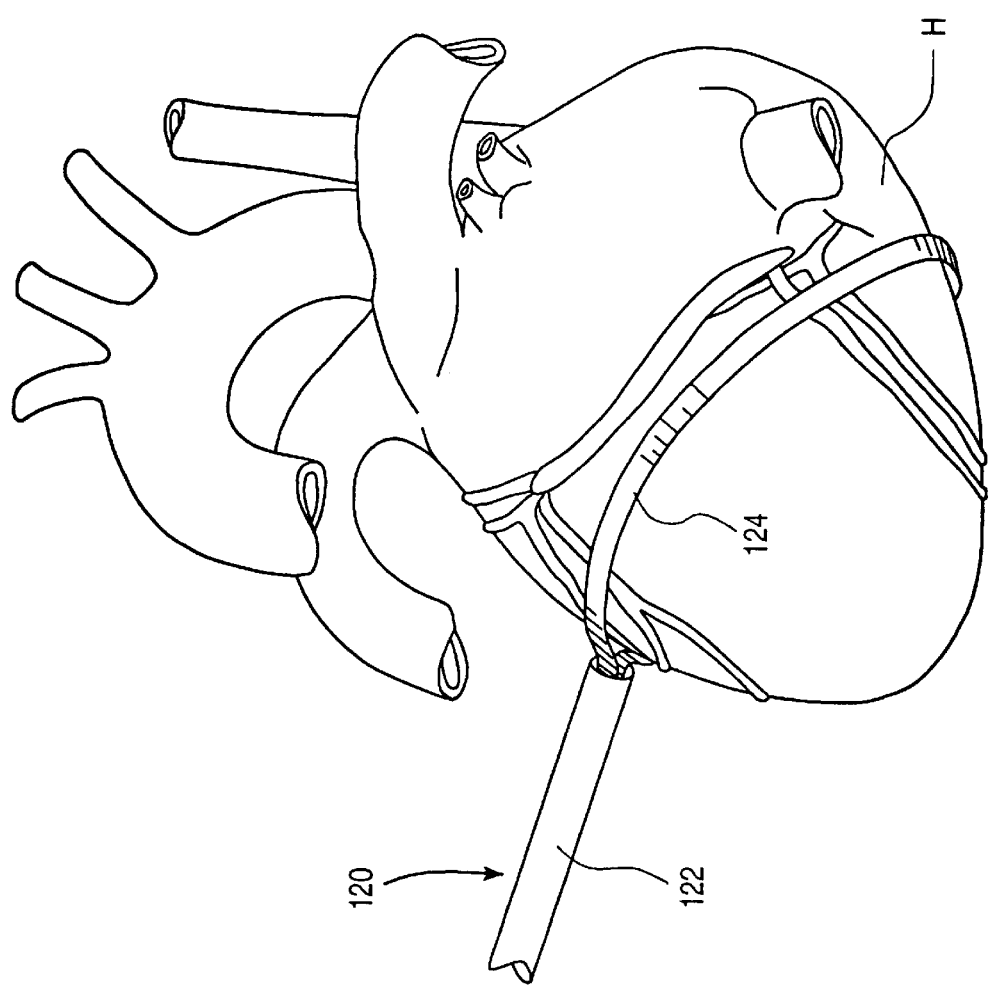
FIG. 10 is a posterior view of a patient's heart illustrating the use of a heart measurement device according to the invention.
Figure 11:
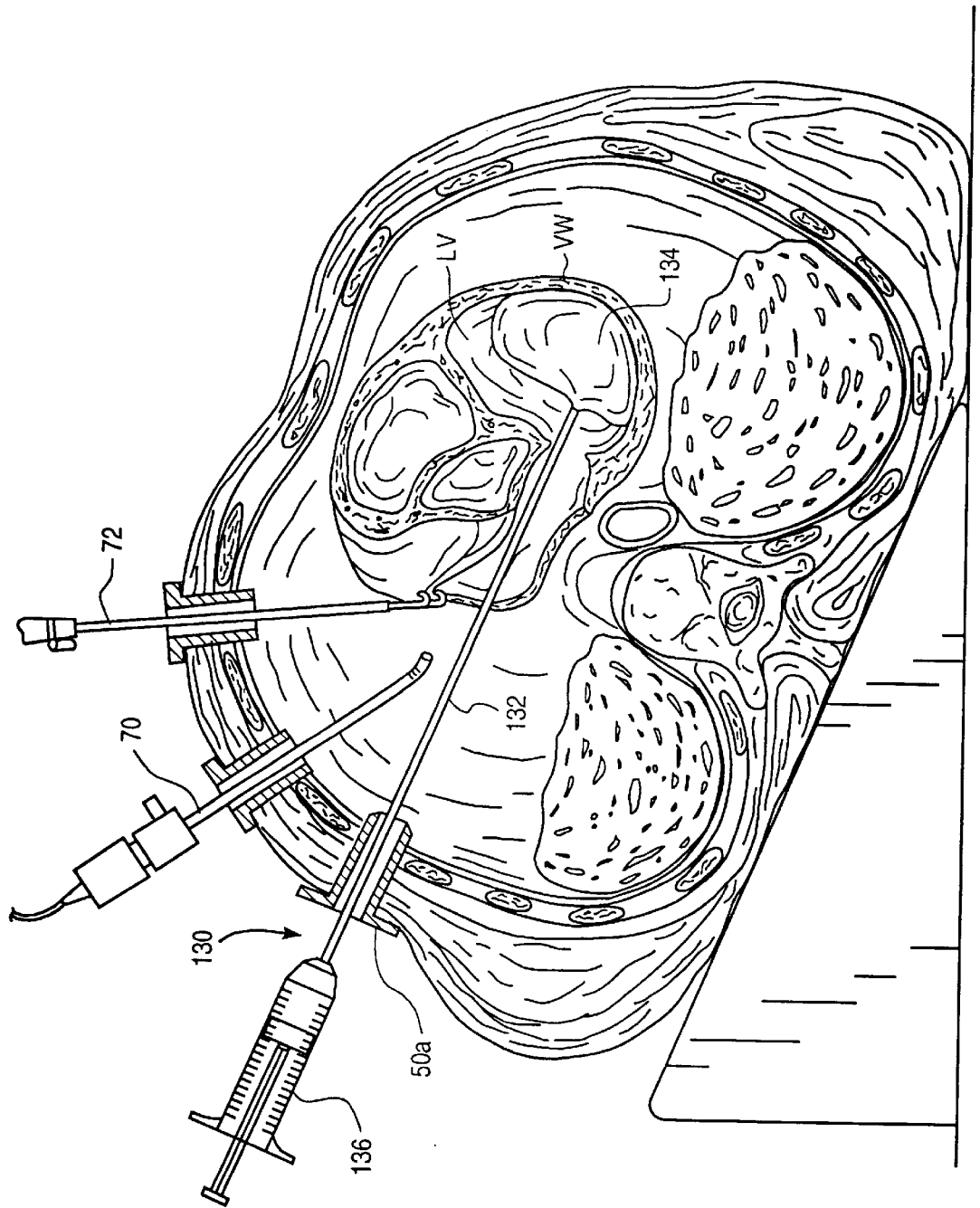
FIG. 11 is a transverse cross-section of a patient's thorax illustrating the use of a left ventricular measurement device according to the invention.

In any of the embodiments of the invention described herein it may desirable to more accurately measure the size of the left ventricle to allow a more precise determination of the amount by which the left ventricle must be reduced. FIGS. 10 and 11 illustrate two alternative embodiments for measuring left ventricular size. In FIG. 10, a thoracoscopic heart measurement device 120 comprises a shaft 122 configured for insertion through a thoracic port between the ribs, and a flexible band 124 extending from the distal end of the shaft to form a loop. Band 124 may be made of a flexible polymer or metal, and extends slidably through an inner lumen in shaft 122 so that the size of the loop may be contracted or expanded by extending or retracting band 124 from the distal end of the shaft. In this way, the loop may be placed around the exterior of the heart H and cinched against the outer wall of the heart. Measurement device 120 is then removed from the chest while maintaining the size of the loop, which may then be measured outside the chest to determine the circumference or diameter of the heart.

An alternative embodiment of a ventricular measurement device 130 is llustrated in FIG. 11. Ventricular measurement device 130 includes a shaft 132 ositionable through a right chest port 50A, through a left atrial incision, through the itral valve, and into the left ventricle LV. Shaft 132 therefore has a length of at least about 20 cm, and usually about 25–40 cm. An elastomeric balloon 134 is attached to the distal end of shaft 132 and has an interior in communication with an inflation lumen extending through shaft 132. An inflation device such as a syringe 136 is attached to the proximal end of shaft 132 in communication with the inflation lumen to facilitate delivery of an inflation fluid into balloon 134. Balloon 134 is of a size large enough to completely occupy the left ventricle, preferably being inflatable to a diameter of 4–12 cm. In this way, measurement device 130 may be introduced into the left ventricle via the left atrium and mitral valve and balloon 134 expanded until it engages the inner ventricular wall. By observing the volume of inflation fluid required to expand the balloon to this size, the approximate volume of the left ventricle may be assessed. In an alternative embodiment, a penetration may be made in the wall of the left ventricle via a port in the left lateral or anterior side of the chest, and balloon 134 inserted directly through the penetration to measure left ventricular volume. A purse string suture may be placed in the heart wall around the penetration to maintain hemostasis around shaft 132.

While the above is a complete description of the preferred embodiments of the invention, it will be understood that various substitutions, modifications, alternatives, and additions will be possible without departing from the scope of the invention, which is defined by the appended claims.

What is claimed is:

1. A method of reshaping a patient's heart muscle, comprising the steps of:

introducing a tissue attaching device into the patient's chest;

engaging a first location on a wall of the patient's left ventricle with the tissue attaching device; and manipulating the tissue attaching device to attach the first location to a second location on a wall of the heart so as to reduce the transverse dimension of the left ventricle, the user's hands remaining outside the patient's chest when manipulating the tissue attaching device.

2. The method of claim 1, further comprising the steps of:

introducing a cutter into the patient's chest, the cutter having a manually operable actuator;

cutting a portion of a patient's left ventricle from the heart with the cutter, the user's hands being outside the patient's chest when actuating the manually operable actuator; and removing the portion of the patient's heart muscle;

the manipulating step being carried out to close an opening in the patient's heart formed by the removing step.

3. The method of claim 2, wherein:

the introducing steps are carried out by passing the cutter and tissue attaching device between adjacent ribs.

4. The method of claim 1, wherein:

the manipulating step is carried out without cutting through the wall of the heart.

5. The method of claim 1, wherein:

the manipulating step comprises folding a section of the heart wall between the first and second locations so as to reduce the size of the left ventricle.

6. The method of claim 1, wherein:

the manipulating step comprises attaching a portion of the left ventricular wall to the interventricular septum.

7. The method of claim 1, further comprising measuring the size of the left ventricle before the step of manipulating using a sizing instrument introduced into the chest while maintaining the hands outside the chest.

8. The method of claim 1, wherein:

the manipulating step is carried out while viewing the heart using a viewing scope.

9. The method of claim 1, wherein:

each of said steps is carried out while maintaining the patient's ribs and sternum intact.

10. The method of claim 1, wherein:

the introducing step is carried out with the tissue attaching device extending between adjacent ribs in the patient.

* * * * *